United States Patent
Bahl et al.

(10) Patent No.: US 11,857,552 B2
(45) Date of Patent: Jan. 2, 2024

(54) 4-[[(7-AMINOPYRAZOLO[1,5-A]PYRIMIDIN-5-YL)AMINO]METHYL]PIPERIDIN-3-OL COMPOUNDS AS CDK INHIBITORS

(71) Applicants: Carrick Therapeutics Limited, Dublin (IE); Cancer Research Technology Limited, London (GB); IP2IPO Innovations Limited, London (GB)

(72) Inventors: Ash Bahl, Dublin (IE); Ed Ainscow, Dublin (IE); Alexander Bondke, Caputh (DE); Anthony G. M. Barrett, Rio de Janeiro (BR); Mihiro Sunose, Nottingham (GB); Jason John Shiers, Nottingham (GB); Kamaldeep Chohan, Nottingham (GB)

(73) Assignee: CARRICK THERAPEUTICS LIMITED, Dublin (IE)

( * ) Notice: Subject to any disclaimer, the term of this patent is extended or adjusted under 35 U.S.C. 154(b) by 597 days.

(21) Appl. No.: 16/648,011

(22) PCT Filed: Sep. 20, 2018

(86) PCT No.: PCT/EP2018/075482
§ 371 (c)(1),
(2) Date: Mar. 17, 2020

(87) PCT Pub. No.: WO2019/057825
PCT Pub. Date: Mar. 28, 2019

(65) Prior Publication Data
US 2020/0345736 A1 Nov. 5, 2020

(30) Foreign Application Priority Data
Sep. 20, 2017 (GB) .................... 1715194

(51) Int. Cl.
*A61K 31/519* (2006.01)
*A61K 33/243* (2019.01)
(Continued)

(52) U.S. Cl.
CPC .......... *A61K 31/519* (2013.01); *A61K 31/138* (2013.01); *A61K 31/337* (2013.01);
(Continued)

(58) Field of Classification Search
CPC .. A61K 31/519; A61K 33/243; A61K 31/138; A61K 31/337; A61K 31/4196;
(Continued)

(56) References Cited

U.S. PATENT DOCUMENTS
8,067,424 B2  11/2011  Jogalekar
9,932,344 B2   4/2018  Bondke
(Continued)

FOREIGN PATENT DOCUMENTS
WO  WO 2001/047897 A1  7/2001
WO  WO 2004/022561 A1  3/2004
(Continued)

OTHER PUBLICATIONS

Alarcon et al., 2009, Cell, vol. 139, pp. 757-769, "Nuclear CDKs Drive Smad Transcriptional Activation and Turnover in BMP and TGF-b Pathways".
Ali et al., 1993, The EMBO Journal, vol. 12, No. 3, pp. 1153-1160, "Modulation of transcriptional activation by ligand dependent phosphorylation of the human oestrogen receptor A/B region".
Ali et al., 2002, Nat. Rev. Cancer, vol. 2, pp. 101-112, "Endocrine-Responsive Breast Cancer and Strategies for Combating Resistance".
(Continued)

*Primary Examiner* — Yan Xiao
(74) *Attorney, Agent, or Firm* — Fish & Richardson P.C.

(57) ABSTRACT

The present invention pertains generally to the field of therapeutic compounds. More specifically the present invention pertains to certain 4-[[(7-aminopyrazolo[1,5-a]pyrimidin-5-yl)amino]methyl]piperidin-3-ol compounds (referred to herein as "APPAMP compounds") that, inter alia, inhibit (e.g., selectively inhibit) CDK (e.g., CDK1, CDK2, CDK4, CDK5, CDK6, CDK7, CDK8, CDK9, CDK10, CDK11, CDK12, CDK13, etc.). The present invention also pertains to pharmaceutical compositions comprising such compounds, and the use of such compounds and compositions, both in vitro and in vivo, to inhibit CDK; and to treat disorders including: disorders that are associated with CDK; disorders that result from an inappropriate activity of a cyclin-dependent kinase (CDK); disorders that are associated with CDK mutation; disorders that are associated with CDK overexpression; disorders that are associated with upstream pathway activation of CDK; disorders that are ameliorated by the inhibition of CDK; proliferative disorders; cancer; viral infections (including HIV); neurodegenerative disorders (including Alzheimer's disease and Parkinson's disease); ischaemia; renal diseases; cardiovascular disorders (including atherosclerosis); and autoimmune disorders (including rheumatoid arthritis). Optionally, the treatment further comprises treatment (e.g., simultaneous or sequential treatment) with a further active agent which is, e.g., an aromatase inhibitor, an anti-estrogen, a Her2 blocker, a cytotoxic chemotherapeutic agent, etc.

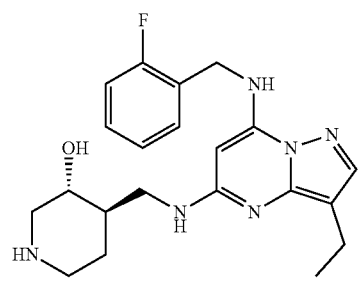

6 Claims, No Drawings

Specification includes a Sequence Listing.

(51) Int. Cl.

| | | |
|---|---|---|
| *A61K 31/138* | (2006.01) | |
| *A61K 31/337* | (2006.01) | |
| *A61K 31/4196* | (2006.01) | |
| *A61K 31/513* | (2006.01) | |
| *A61K 31/517* | (2006.01) | |
| *A61K 31/565* | (2006.01) | |
| *A61K 31/5685* | (2006.01) | |
| *A61K 31/675* | (2006.01) | |
| *A61K 31/704* | (2006.01) | |
| *A61K 31/7068* | (2006.01) | |
| *C07D 487/04* | (2006.01) | |
| *A61K 39/395* | (2006.01) | |

(52) U.S. Cl.
CPC ........ *A61K 31/4196* (2013.01); *A61K 31/513* (2013.01); *A61K 31/517* (2013.01); *A61K 31/565* (2013.01); *A61K 31/5685* (2013.01); *A61K 31/675* (2013.01); *A61K 31/704* (2013.01); *A61K 31/7068* (2013.01); *A61K 33/243* (2019.01); *A61K 39/3955* (2013.01); *C07D 487/04* (2013.01)

(58) Field of Classification Search
CPC .. A61K 31/513; A61K 31/517; A61K 31/565; A61K 31/5685; A61K 31/675; A61K 31/704; A61K 31/7068; A61K 39/3955; C07D 487/04
USPC ...................................................... 424/133.1
See application file for complete search history.

(56) References Cited

U.S. PATENT DOCUMENTS

| 10,414,772 B2* | 9/2019 | Bondke ................. A61P 35/04 |
|---|---|---|
| 10,927,119 B2* | 2/2021 | Bondke ................. A61P 35/04 |
| 2010/0261683 A1 | 10/2010 | Jogalekar |
| 2016/0362410 A1 | 8/2016 | Bondke |

FOREIGN PATENT DOCUMENTS

| WO | WO 2004/069162 A2 | 8/2004 |
|---|---|---|
| WO | WO 2004/076458 A1 | 9/2004 |
| WO | WO 2004/087707 A1 | 10/2004 |
| WO | WO 2005/000838 A1 | 1/2005 |
| WO | WO 2008/151304 A1 | 12/2008 |
| WO | WO 2011/068667 A1 | 6/2011 |
| WO | WO 2012/059932 A1 | 5/2012 |
| WO | WO 2013/128028 A1 | 9/2013 |
| WO | WO 2013/128029 A1 | 9/2013 |
| WO | WO 2015/124941 | 8/2015 |
| WO | WO 2015/124941 A1 | 8/2015 |
| WO | WO 2019/057825 A1 | 3/2019 |

OTHER PUBLICATIONS

Ali et al, 2011, Annu. Rev. Med., vol. 62, pp. 217-232, "Antiestrogens and Their Therapeutic Applications in Breast Cancer and Other Diseases".
Bacher et al., 2004, Current Pharmaceutical Design vol. 10, pp. 2827-2837, "The NF-kB Pathway as a Potential Target for Autoimmune Disease Therapy".
Bartkowiak et al., 2010, Gene Dev., vol. 24, pp. 2303-2316, "CDK12 is a transcription elongation associated CTD kinase, the metazoan ortholog of yeast Ctk1".
Bastien et al., 2000, J. Biol. Chem., vol. 275, No. 29, pp. 21896-21904, "TFIIH Interacts with the Retinoic Acid Receptor γ and Phosphorylates Its AF-1-activating Domain through cdk7".
Blazek et al., 2011, Gene Dev., vol. 25, pp. 2158-2172, "The Cyclin K/Cdk12 complex maintains genomic stability via regulation of expression of DNA damage response genes".
Borg et al., 2000, JNCI, vol. 92, No. 15, pp. 1260-1266, "High Frequency of Multiple Melanomas and Breast and Pancreas Carcinomas in CDKN2A Mutation-Positive Melanoma Families".
Chen et al., 2000, Molecular Cell, vol. 6, pp. 127-137, "Activation of Estrogen Receptor α by S118 Phosphorylation Involves a Ligand-Dependent Interaction with TFIIH and Participation of CDK7".
Chen et al., 2002, Oncogene, vol. 21, pp. 4921-4931, "Phosphorylation of human estrogen receptor α at serine 118 by two distinct signal transduction pathways revealed by phosphorylation-specific antisera".
Cheng et al., 2012, Mol. Cell. Biol., vol. 32, No. 22, pp. 4691-4704. "Interaction of Cyclin-Dependent Kinase 12/CrkRS with Cyclin K1 Is Required for the Phosphorylation of the C-Terminal Domain of RNA Polymerase II".
Chymkowitch et al., 2011, EMBO J., vol. 30, No. 3, pp. 468-479, "The phosphorylation of the androgen receptor by TFIIH directs the ubiquitin/proteasome process".
Claudio et al., 2006, J. Cell. Physiol., vol. 208, pp. 602-612, "Cdk9 Phosphorylates p53 on Serine 392 Independently of CKII".
Corlu et al., 2012, Int. J. Hepatol., Article ID 689324, 17 pages, "Regulation of the G1/S Transition in Hepatocytes: Involvement of the Cyclin-Dependent Kinase Cdk1 in the DNA Replication".
Cuzick et al., 2010, Lancet Oncol., vol. 11, pp. 1135-1141, "Effect of anastrozole and tamoxifen as adjuvant treatment for early-stage breast cancer: 10-year analysis of the ATAC Trial".
Drogat et al., 2012, Cell Rep., vol. 2, pp. 1068-1076, "Cdk11-CyclinL Controls the Assembly of the RNA Polymerase II Mediator Complex".
Dhariwala et al., 2008, Cell. Mol. Neurobiol., vol. 28, pp. 351-369, "An Unusual Member of the Cdk Family: Cdk5".
Fisher et al., 1994, Cell, vol. 78, pp. 713-724, "A Novel Cyclin Associates with MO15/CDK7 to Form the CDK-Activating Kinase".
GB Search Report for GB 1403093.6, dated Sep. 12, 2014, 5 pages.
GB Search Report for GB 1715194.5, dated Jun. 5, 2018, 5 pages.
Ganuza et al., 2012, EMBO J., vol. 31, pp. 2498-2510, "Genetic inactivation of Cdk7 leads to cell cycle arrest and induces premature aging due to adult stem cell exhaustion".
Gijsen et al., 2008, Tetrahedron, vol. 64, pp. 2456-2464, "Development of two diastereoselective routes towards trans-4-aminomethyl-piperidin-3-ol building blocks".
Gordon et al., 2010, Mol. Endocrinol., vol. 24, No. 12, pp. 2267-2280, "CDK9 Regulates AR Promoter Selectivity and Cell Growth through Serine 81 Phosphorylation".
Hamada et al., 1996, Biochim. Biophys. Acta., vol. 1310, pp. 149-156, "Protein kinase C inhibits the CAK-CDK2 cyclin-dependent kinase cascade and G1/S cell cycle progression in human diploid fibroblasts".
Hansson, 2008, Surg. Clin. North Am., vol. 88, pp. 897-916, "Familial Melanoma".
Hansson, 2010, Adv. Exp. Med. Biol., vol. 685, Chapter 13, pp. 134-145, "Familial Cutaneous Melanoma".
Hong et al., 1997, Tetrahedron Lett., vol. 38, No. 32, pp. 5607-5610, "Palladium Catalyzed Amination of 2-Chloro-1,3-Azole Derivatives: Mild Entry to Potent $H_1$- Antihistaminic Norastemizole".
Hong et al., 2018, J. Cell. Mol. Med. vol. 22, pp. 1292-1301. "CDK7 inhibition suppresses rheumatoid arthritis inflammation via blockage of NF- κb activation and IL-1b/IL-6 secretion".
International Search Report and Written Opinion of the International Searching Authority for PCT/GB2015/050494 dated Apr. 14, 2015, 9 pages.
International Preliminary Report on Patentability for PCT/GB2015/050494 dated Aug. 23, 2016, 6 pages.
International Search Report and Written Opinion of the International Searching Authority for PCT/EP2018/075482 dated Nov. 20, 2018, 12 pages.
Iorns et al., 2008, Cancer Cell, vol. 13, pp. 91-104, "Identification of CDK10 as an Important Determinant of Resistance to Endocrine Therapy for Breast Cancer".
Johnston et al., 2003, Nat. Rev. Cancer, vol. 3, pp. 821-831, "Aromatase Inhibitors For Breast Cancer: Lessons From The Laboratory".
Jones et al., 2007, Cell, vol. 128, pp. 683-692, "The Epigenomics of Cancer".

(56) References Cited

OTHER PUBLICATIONS

Knockaert et al., 2002, Trends Pharmacol. Sci., vol. 23, No. 9, pp. 417-425, "Pharmacological inhibitors of cyclin-dependent kinases".
Ko et al., 1997, Mol. Cell. Biol., vol. 17, No. 12, pp. 7220-7229 p53 Is Phosphorylated by CDK7-Cyclin H in a p36$^{MAT1}$-Dependent Manner.
Kolb et al., 1994, Chem. Rev., vol. 94, pp. 2483-2547, "Catalytic Asymmetric Dihydroxylation".
Kosugi et al., 2012, J. Med. Chem., 55(15):6700-6715, "Mitogen-Activated Protein Kinase-Activated Protein Kinase 2 (MAPKAP-K2) as an Antiinflammatory Target: Discovery and In Vivo Activity of Selective Pyrazolo[1,5-α]pyrimidine Inhibitors Using a Focused Library and Structure-Based Optimization Approach".
Larochelle et al., 2007, Mol. Cell, vol. 25, pp. 839-850, "Requirements for Cdk7 in the Assembly of Cdk1/Cyclin B and Activation of Cdk2 Revealed by Chemical Genetics in Human Cells".
Larochelle et al., 2012, Nat. Struct. Mol. Biol., vol. 19, No. 11, pp. 1108-1115, "Cyclin-dependent kinase control of the initiation-to-elongation switch of RNA polymerase II".
Lu et al., 1992, Nature, pp. 358, pp. 641-645, "Human general transcription factor IIH phosphorylates the C-terminal domain of RNA polymerase II".
Lu et al., 1997, Mol. Cell. Biol., vol. 17, No. 10, pp. 5923-5934, "The CDK7-cycH-p36 Complex of Transcription Factor IIH Phosphorylates p53, Enhancing Its Sequence-Specific DNA Binding Activity In Vitro".
Malumbres et al., 2001, Nat. Rev. Cancer, vol. 1, pp. 222-231, "To Cycle or Not to Cycle: A Critical Decision in Cancer".
Malumbres et al., 2009, Nat. Cell Biology, vol. 11, pp. 1275-1276, "Cyclin-dependent kinases: a family portrait".
Malumbres et al., 2009, Nat. Rev. Cancer, vol. 9, pp. 153-166, "Cell cycle, CDKs and cancer: a changing paradigm".
Marshall et al., 2006, Nephron. Exp. Nephrol., vol. 102, No. 2, pp. e39-e48, "Cell Cycle and Glomerular Disease: A Minireview".
Monaco et al., 2005, Front. Biosci., vol. 10, No. 1, pp. 143-159, "Role of Protein Kinases In Neurodegenerative Disease: Cyclin-Dependent Kinases in Alzheimer's Disease".
Morgan, 1995, Nature, vol. 374, pp. 131-134, "Principles of CDK regulation".
Nagel et al., 1984, Angew. Chem. Int. Ed. Eng. vol. 23, No. 6, pp. 435-436 (corresponding to Angew. Chem., vol. 96, No. 6, pp. 425-426), "Asymmetric Hydrogenation of a-(Acetylamino)cinnamic Acid with a Novel Rhodium Complex; the Design of an Optimal Ligand".
Ortega et al., 2002, Biochim. Biophys. Acta., vol. 1602, pp. 73-87, "Cyclin D-dependent kinases, INK4 inhibitors and cancer".
Osborne et al., 2011, Annu. Rev. Med., vol. 62, pp. 233-247, "Mechanisms of Endocrine Resistance in Breast Cancer".
Osborne, 1998, N. Engl. J. Med., vol. 339, No. 22, pp. 1609-1618, "Tamoxifen in the Treatment of Breast Cancer".
Peterson et al., 1991, J. Med. Chem., vol. 34, pp. 2787-2797, "Synthesis and Biological Evaluation of 4-Purinylpyrrolidine Nucleosides".
Pines, 1995, Biochem. J., vol. 308, pp. 697-711, "Cyclins and cyclin-dependent kinases: a biochemical view".
Radhakrishnan et al., 2006, Cell Cycle, vol. 5, No. 5, pp. 519-521, "CDK9 Phosphorylates p53 on Serine Residues 33, 315 and 392".
Remuzon, 1996, Tetrahedron, vol. 52, No. 44, 13803-13835, "Trans-4-Hydroxy.L-Proline, a Useful and Versatile Chiral Starting Block".
Rochette-Egly et al., 1997, Cell, vol. 90, pp. 97-107. "Stimulation of RARα Activation Function AF-1 through Binding to the General Transcription Factor TFIIH and Phosphorylation by CDK7".
Serizawa et al., 1995, Nature, vol. 374, pp. 280-282, "Association of Cdk-activating kinase subunits with transcription factor TFIIH".
Sherr et al., 1995, Genes Dev., vol. 9, pp. 1149-1163, "Inhibitors of mammalian G$_1$ cyclin-dependent kinases".
Shiekhattar et al., 1995, Nature, vol. 374, pp. 283-287, "Cdk-activating kinase complex is a component of human transcription factor TFIIH".
Skehan et al., 1990, J. Natl. Cancer Inst., vol. 82, No. 13, pp. 1107-1112, "New Colorimetric Cytotoxicity Assay for Anticancer-Drug Screening".
Wang et al., 2008, Trends Pharmacol. Sci., vol. 29, No. 6, pp. 302-313, "Cyclin-dependent kinase 9: a key transcriptional regulator and potential drug target in oncology, virology and cardiology".
Xu et al., 2011, J. Genet. Genomics, vol. 38, pp. 439-452, "Dysregulation of CDK8 and Cyclin C in tumorigenesis".
Xu et al., 2011, Tetrahedron Lett., vol. 52, pp. 3266-3270, "An improved synthesis of 2-oxa-7-azaspiro[3,5]nonane and analogs as novel reagents in medicinal chemistry".
Yankulov et al., 1995, J. Biol. Chem., vol. 270, No. 41, pp. 23922-23925, "The Transcriptional Elongation Inhibitor 5,6-Dichloro-1-β-D-ribofuranosylbenzimidazole Inhibits Transcription Factor IIH-associated Protein Kinase".
Yu et al., 2012, Oncol. Rep., vol. 27, pp. 1266-1276, "CDK10 functions as a tumor suppressor gene and regulates survivability of biliary tract cancer cells".
Zuo et al., 1996, Nat. Genet., vol. 12, pp. 97-99, "Germline mutations in the p16$^{INK4a}$ binding domain of CDK4 in familial melanoma".
Examination Report for Indian App. No. 202017013406, dated Sep. 28, 2021, 6 pgs.
Martin et al., 2013 ACS Chemical Biology, vol. 8, pp. 2360-2365, "Cyclin-Dependent Kinase Inhibitor Dinaciclib Interacts with the Acetyl- Lysine Recognition Site of Bromodomains".
Paruch, et al., 2007, Bioorganic & Medicinal Chemistry Letters, vol. 17, pp. 6220-6223, "Pyrazolo[1,5-a]pyrimidines as orally available inhibitors of cyclin-dependent kinase 2".
Paruch, et al., 2010, ACS Medicinal Chemistry Letters, vol. 1, pp. 204-208, "Discovery of Dinaciclib (SCH 727965): A Potent and Selective Inhibitor of Cyclin-Dependent Kinases".
International Search Report and Written Opinion for PCT/EP2018/075482 dated Nov. 20, 2018, 8 pages.
Gottesman et al., "Multidrug resistance in cancer: role of ATP-dependent transporters," Nature Reviews Cancer, Jan. 1, 2002, 2(1):48-58.

* cited by examiner

4-[[(7-AMINOPYRAZOLO[1,5-A]PYRIMIDIN-5-YL)AMINO]METHYL]PIPERIDIN-3-OL COMPOUNDS AS CDK INHIBITORS

RELATED APPLICATION

This application claims priority to and is a 35 U.S.C. § 371 national phase application of PCT/EP2018/075482 (WO2019/057825A1), filed on Sep. 20, 2018. PCT/EP2018/075482 is related to, and claims priority of, Great Britain patent application number 1715194.5, filed Sep. 20, 2017, the contents of which are incorporated herein by reference in their entirety.

SEQUENCE STATEMENT

Incorporated by reference herein in its entirety is the Sequence Listing text document entitled "0206-276_PCT-US" created Jun. 17, 2020, size of 560 bytes.

TECHNICAL FIELD

The present invention pertains generally to the field of therapeutic compounds. More specifically the present invention pertains to certain 4-[[(7-aminopyrazolo[1,5-a]pyrimidin-5-yl)amino]methyl]piperidin-3-ol compounds (referred to herein as "APPAMP compounds") that, inter alia, inhibit (e.g., selectively inhibit) CDK (e.g., CDK1, CDK2, CDK4, CDK5, CDK6, CDK7, CDK8, CDK9, CDK10, CDK11, CDK12, CDK13, etc.). The present invention also pertains to pharmaceutical compositions comprising such compounds, and the use of such compounds and compositions, both in vitro and in vivo, to inhibit CDK; and to treat disorders including: disorders that are associated with CDK; disorders that result from an inappropriate activity of a cyclin-dependent kinase (CDK); disorders that are associated with CDK mutation; disorders that are associated with CDK overexpression; disorders that are associated with upstream pathway activation of CDK; disorders that are ameliorated by the inhibition of CDK; proliferative disorders; cancer; viral infections (including HIV); neurodegenerative disorders (including Alzheimer's disease and Parkinson's disease); ischaemia; renal diseases; cardiovascular disorders (including atherosclerosis); and autoimmune disorders (including rheumatoid arthritis). Optionally, the treatment further comprises treatment (e.g., simultaneous or sequential treatment) with a further active agent which is, e.g., an aromatase inhibitor, an anti-estrogen, a Her2 blocker, a cytotoxic chemotherapeutic agent, etc.

BACKGROUND

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Cyclin-Dependent Protein Kinase (CDK)

Cyclin-dependent protein kinases (CDK) are the catalytic subunits of a family of 21 serine/threonine protein kinases (see, e.g., Malumbres et al., 2009), some of which control progression of the cell through the stages of growth, DNA replication and mitosis (see, e.g., Pines, 1995; Morgan, 1995). Activation of specific CDKs is required for appropriate progression through the different stages of the cell cycle and entry into the next stage of the cell cycle. CDK4 and CDK6 are required for progression through the growth (G1) phase, CDK2 in the DNA synthesis (S phase) and CDK1 for mitosis and cell division (M phase). Regulation of the activity of the cell cycle CDKs is pivotal for correct timing of progression of the cell through the stages of the cell cycle and their activities are regulated at many levels, including complex formation with specific cyclins (A, B, D and E class cyclins; these cyclins are synthesized and degraded through the stages of the cell cycle), CDK inhibitors (CDKI), in particular CIP/KIP and INK-type CDKIs (see, e.g., Sherr et al., 1995), as well as phosphorylation and dephosphorylation at specific residues. The phosphorylation status of a specific threonine residue in the activation loop, the so-called T-loop, is a key modification for the activity of cell cycle CDKs (see, e.g., Fisher et al., 1994).

De-regulation of CDK activity is an important component of many disease states, generally through elevated and/or inappropriate activation, as CDKs themselves are infrequently mutated. Rare examples of mutations in cell cycle CDKs include CDK4 families with hereditary melanoma that result in insensitivity to the INK4 CDKIs (see, e.g., Zuo et al, 1996). Inactivating mutations in the CDKN2A gene, which encodes for p16INK4 and p14ARF CDKIs, are more common in hereditary melanoma (see, e.g., Hansson, 2010), these mutations also being associated with greater incidence of breast and pancreatic cancer in affected families (see, e.g., Borg et al., 2000). CDK4 and CDK6 can be amplified and/or overexpressed in cancer, their cyclin effectors, D-type cyclins, are also often amplified and/or over-expressed, whilst the CDK4/CDK6 inhibitors (INK4 genes) are frequently deleted in many cancer types and/or undergo epigenetic silencing (see, e.g., Ortega et al., 2002). E-type cyclins interact with CDK2 for its activity and are frequently over-expressed in cancer, whilst the p21 and p27 inhibitory proteins that act on CDK2, as well as CDK1, are epigenetically silenced in cancer (see, e.g., Malumbres et al., 2001; Jones et al., 2007). Up-regulation of the activities of cell cycle CDKs is therefore integral to cancer development and progression.

CDK7, another member of the CDK family, which complexes with cyclin H and MAT1, phosphorylates the cell cycle CDKs in the activation of T-loop, to promote their activities (see, e.g., Fisher et al., 1994). As such, it has been proposed that inhibiting CDK7 would provide a potent means of inhibiting cell cycle progression, which may be especially relevant given that there is compelling evidence from gene knockout studies in mice for lack of an absolute requirement for CDK2, CDK4 and CDK6 for the cell cycle, at least in most cell types (see, e.g., Malumbres et al., 2009), whilst different tumors appear to require some, but be independent of other interphase CDKs (CDK2, CDK4, CDK6). Recent genetic and biochemical studies have confirmed the importance of CDK7 for cell cycle progression (see, e.g., Larochelle et al., 2007; Ganuza et al., 2012).

In addition to its role as the CDK Activating Kinase (CAK), CDK7/cyclin H/MAT1, in complex with the basal transcription factor TFIIH, phosphorylates RNA polymerase II (PolII) in its C-terminal domain (CTD) (see, e.g., Lu et al., 1995; Serizawa et al., 1995). CDK9, another member of the family, is also required for PolII CTD phosphorylation. The PolII CTD is comprised of a seven amino acid repeat having the sequence Tyrosine-Serine-Proline-Threonine-Serine-Proline-Serine (YSPTSPS; SEQ ID NO: 1), 52 YSPTSPS heptad repeats being present in the mammalian PolII CTD. Phosphorylation of serine-2 (S2) and serine-5 (S5) by CDK7 and CDK9 is required for release of PolII from the gene promoter at initiation of transcription. CDK7 appears to act upstream of CDK9, phosphorylation of S5 phosphorylation by CDK7 preceding S2 phosphorylation by CDK9 (see, e.g., Larochelle et al., 2012). Transcriptional inhibitors such as flavopiridol, as well as CDK inhibitors that inhibit CDK7 and CDK9 demonstrate the potential utility of CDK7 and CDK9 inhibition in cancer (see, e.g., Wang et al., 2008). In addition to their action in phosphorylating the PolII CTD, CDK7 and CDK9 have been implicated in regulating the activities of a number of transcription factors, including the breast cancer associated estrogen receptor (ER) (see, e.g., Chen et al., 2000), retinoid receptors (see, e.g., Rochette-Egly et al., 1997; Bastien et al., 2000), the androgen receptor (see, e.g., Chymkowitch et al., 2011; Gordon et al., 2010), as well as the tumor suppressor p53 (Lu et al., 1997; Ko et al., 1997; Radhakrishnan et al., 2006; Claudio et al., 2006). CDK8, a component of the mediator complex that regulates gene transcription, through a mechanism involving interaction between transcription factors and the PolII basal transcription machinery, also phosphorylates transcription factors to regulate their activities (see, e.g., Alarcon et al., 2009). CDK8 also appears to be important for regulating transcription reinitiation. The importance of CDK8 in cancer is highlighted by the finding that the CDK8 gene is amplified in 40-60% of colorectal cancers, whilst its cyclin partner, cyclin c, is upregulated in many cancer types, whilst functional studies are supportive of an oncogenic role for CDK8 in cancer (see, e.g., Xu et al., 2011). A potential role for CDK11 in regulating mediator activity has been described, indicating a role for CDK11 in transcription regulation (see, e.g., Drogat et al., 2012), whilst their ability to phosphorylate S2 the PolII CTD also implicates CDK12 and CDK13 in transcription; CDK12 is also implicated in maintenance of genome stability (see, e.g., Bartkowiak et al., 2010; Blazek et al., 2011; Cheng et al., 2012).

In addition to the great deal of evidence implicating the above and other CDKs (e.g., CDK10; see, e.g., Lorns et al., 2008; Yu et al., 2012) in cancer, CDKs are also important in viral infections including HIV (see, e.g., Knockeart et al., 2002), neurodegenerative disorders including Alzheimer's and Parkinson's disease (of particular note here is CDK5, see, e.g., Monaco et al., 2005; Faterna et al., 2008), ischaemia, proliferative disorders, including renal diseases (see, e.g., Marshall et al., 2006) and cardiovascular disorders including atherosclerosis, and autoimmune disorders, including rheumatoid arthritis. Indeed, it has been shown that CDK7 inhibition suppresses rheumatoid arthritis inflammation via blockage of NF-κB activation and IL-1β/IL-6 secretion (see, e.g., Hong et al., 2018). Furthermore, the ability of CDK7 inhibition to prevent the NF-κB signaling pathway points to a potentially broader ability for CDK7 inhibitors to treat a range of autoimmune diseases (see, e.g., Bacher et al., 2004).

The development of small molecule CDK inhibitors provides a potentially powerful approach in the treatment of many human diseases, in particular cancer. Thus inhibition of cell cycle progression may be achieved through the development of selective CDK1 inhibitors (as CDK1 appears to be indispensible for the cell cycle) or selective CDK7 inhibitors (as CDK7 regulates the cell cycle CDKs) or with inhibitors with activity against all of the cell cycle CDKs. Some evidence indicates that selective CDK4/CDK6 or CDK2 inhibitors may have utility for specific conditions (e.g., CDK4/CDK6 in haematological malignancies and CDK2 in glioblastomas or osteosarcomas), and so development of selective inhibitors for these CDKs may be of utility, the selectivity perhaps aiding toxicity issues.

Known Compounds

Bondke et al., 2015, describes certain pyrazolo[1,5-a]pyrimidine-5,7-diamine compounds as CDK inhibitors, including, for example, the following compound (referred to therein as PPDA-001):

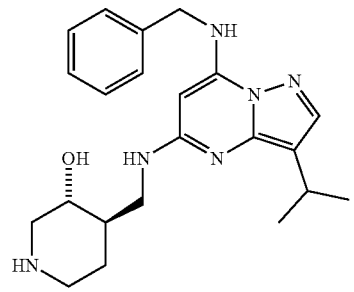 [SMILES: CC(C)c1cnn2c(NCc3ccccc3)cc(NC[C@H]3CCNC[C@@H]3O)nc12]

New Compounds with Improved Properties

The APPAMP compounds described herein are surprisingly and unexpectedly better than known structurally similar compounds, for example, as shown in Bondke et al., 2015.

For example, the APPAMP compounds described herein provide substantial improvements in respect of one or more important and advantageous properties, including: improved CDK7 potency; improved selectivity for CDK7 vs. CDK2; improved free fraction in human plasma; and reduced MDCK-MDR1 and/or MDCK-BCRP efflux.

Without wishing to be bound to any particular theory, the inventors believe that the particular combinations of substituents and their positions give rise to the extraordinary properties of the claimed compounds.

SUMMARY OF THE INVENTION

One aspect of the invention pertains to certain 4-[[(7-aminopyrazolo[1,5-a]pyrimidin-5-yl)amino]methyl]piperidin-3-ol compounds (referred to herein as "APPAMP compounds"), as described herein.

Another aspect of the invention pertains to a composition (e.g., a pharmaceutical composition) comprising an APPAMP compound, as described herein, and a pharmaceutically acceptable carrier or diluent.

Another aspect of the invention pertains to a method of preparing a composition (e.g., a pharmaceutical composition) comprising the step of mixing an APPAMP compound, as described herein, and a pharmaceutically acceptable carrier or diluent.

Another aspect of the present invention pertains to a method of inhibiting CDK (e.g., CDK1, CDK2, CDK4, CDK5, CDK6, CDK7, CDK8, CDK9, CDK10, CDK11, CDK12, CDK13, etc.) function (e.g., in a cell), in vitro or in vivo, comprising contacting the cell with an effective amount of an APPAMP compound, as described herein.

Another aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of an APPAMP compound, as described herein.

Another aspect of the present invention pertains to an APPAMP compound as described herein for use in a method of treatment of the human or animal body by therapy, for example, for use a method of treatment of a disorder (e.g., a disease) as described herein.

Another aspect of the present invention pertains to use of an APPAMP compound, as described herein, in the manufacture of a medicament, for example, for use in a method of treatment, for example, for use a method of treatment of a disorder (e.g., a disease) as described herein.

Another aspect of the present invention pertains to a method of treatment, for example, a method of treatment of a disorder (e.g., a disease) as described herein, comprising administering to a subject in need of treatment a therapeutically-effective amount of an APPAMP compound, as described herein, preferably in the form of a pharmaceutical composition.

In one embodiment, the treatment further comprises treatment (e.g., simultaneous or sequential treatment) with a further active agent which is, e.g., an aromatase inhibitor, an anti-estrogen, a Her2 blocker, a cytotoxic chemotherapeutic agent, etc., as described herein.

Another aspect of the present invention pertains to a kit comprising (a) an APPAMP compound, as described herein, preferably provided as a pharmaceutical composition and in a suitable container and/or with suitable packaging; and (b) instructions for use, for example, written instructions on how to administer the compound.

Another aspect of the present invention pertains to an APPAMP compound obtainable by a method of synthesis as described herein, or a method comprising a method of synthesis as described herein.

Another aspect of the present invention pertains to an APPAMP compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

One aspect of the present invention relates to certain compounds which are related to pyrazolo[1,5-a]pyrimidine-5,7-diamine:

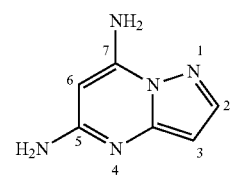

More specifically, the compounds are related to 4-[[(7-aminopyrazolo[1,5-a]pyrimidin-5-yl)amino]methyl]piperidin-3-ol:

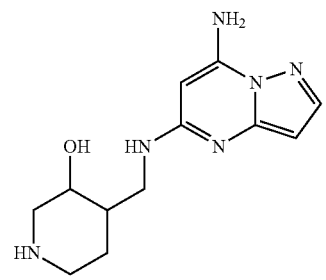 [SMILES: Nc1cc(NCC2CCNCC2O)nc2ccnn12]

Yet more specifically, the compounds are certain substituted 4-[[(7-aminopyrazolo[1,5-a]pyrimidin-5-yl)amino]methyl]piperidin-3-ol compounds that have the following structural formula, wherein —$R^3$, —$R^6$, and —$R^7$ are as defined herein:

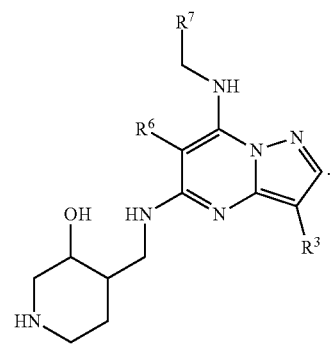

Thus, one aspect of the present invention is a compound selected from compounds of the following formulae, or a pharmaceutically acceptable salt, hydrate, or solvate thereof (for convenience, collectively referred to herein as "4-[[(7-aminopyrazolo[1,5-a]pyrimidin-5-yl)amino]methyl]piperidin-3-ol compounds" and "APPAMP compounds"):

| Pat Code | Name | Structure |
|---|---|---|
| APPAMP-001 | (3R,4R)-4-(((3-ethyl-7-((2-fluorobenzyl)amino)pyrazolo[1,5-a]pyrimidin-5-yl)amino)methyl)piperidin-3-ol | 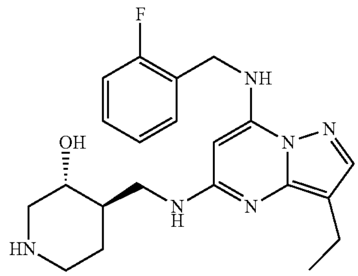 [SMILES: CCc1cnn2c(NCc3ccccc3F)cc(NC[C@H]3CCNC[C@@H]3O)nc12] |
| APPAMP-002 | (3R,4R)-4-(((7-(benzylamino)-3-cyclopropylpyrazolo[1,5-a]pyrimidin-5-yl)amino)methyl)piperidin-3-ol | 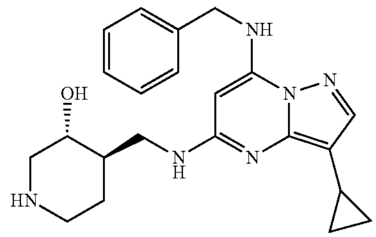 [SMILES: O[C@H]1CNCC[C@@H]1CNc1cc(NCc2ccccc2)n2ncc(C3CC3)c2n1] |
| APPAMP-003 | 3-(((3-ethyl-5-((((3R,4R)-3-hydroxypiperidin-4-yl)methyl)amino)pyrazolo[1,5-a]pyrimidin-7-yl)amino)methyl)benzonitrile | 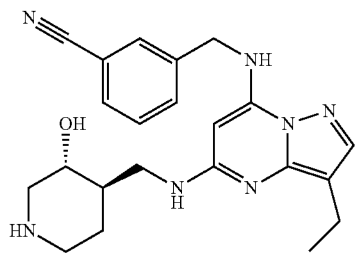 [SMILES: CCc1cnn2c(NCc3cccc(C#N)c3)cc(NC[C@H]3CCNC[C@@H]3O)nc12] |
| APPAMP-004 | 3-(((6-chloro-3-ethyl-5-((((3R,4R)-3-hydroxypiperidin-4-yl)methyl)amino)pyrazolo[1,5-a]pyrimidin-7-yl)amino)methyl)benzonitrile | 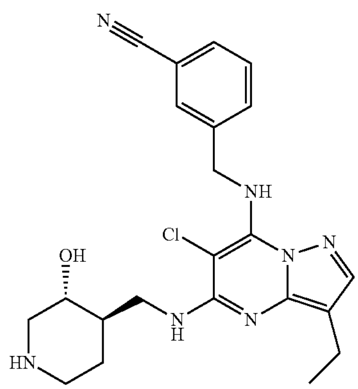 [SMILES: CCc1cnn2c(NCc3cccc(C#N)c3)c(Cl)c(NC[C@H]3CCNC[C@@H]3O)nc12] |

Substantially Purified Forms

One aspect of the present invention pertains to APPAMP compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless otherwise specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to a equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Isomers

Certain compounds may exist in one or more particular geometric, optical, enantiomeric, diastereoisomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

A reference to a class of structures may well include structurally isomeric forms falling within that class (e.g., $C_{1-7}$ alkyl includes n-propyl and iso-propyl; butyl includes n-, iso-, sec-, and tert-butyl; methoxyphenyl includes ortho-, meta-, and para-methoxyphenyl). However, reference to a specific group or substitution pattern is not intended to include other structural (or constitutional isomers) which differ with respect to the connections between atoms rather than by positions in space. For example, a reference to a methoxy group, —$OCH_3$, is not to be construed as a reference to its structural isomer, a hydroxymethyl group, —$CH_2OH$. Similarly, a reference specifically to ortho-chlorophenyl is not to be construed as a reference to its structural isomer, meta-chlorophenyl.

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro. A reference herein to one tautomer is intended to encompass both tautomers.

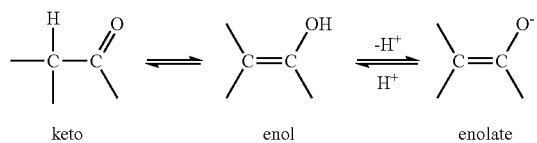

keto          enol          enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group, which may be anionic (e.g., —COOH may be —$COO^-$), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$ as well as the ammonium ion (i.e., $NH_4^+$). Examples of suitable organic cations include, but are not limited to substituted ammonium ions (e.g., $NH_3R^+$, $NH_2R_2^+$, $NHR_3^+$, $NR_4^+$), for example, where each R is independently linear or branched saturated $C_{1-18}$alkyl, $C_{3-8}$ cycloalkyl, $C_{3-8}$ cycloalkyl-$C_{1-6}$alkyl, and phenyl-$C_{1-6}$ alkyl, wherein the phenyl group is optionally substituted. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group, which upon protonation may become cationic (e.g., —$NH_2$ may become —$NH_3^+$), then a salt may be formed with a suitable anion.

For example, if a parent structure contains a cationic group (e.g., —$NMe_2^+$), or has a functional group, which upon protonation may become cationic (e.g., —$NH_2$ may become —$NH_3^+$), then a salt may be formed with a suitable anion. In the case of a quaternary ammonium compound a counter-anion is generally always present in order to balance the positive charge. If, in addition to a cationic group (e.g., —$NMe_2^+$, —$NH_3^+$), the compound also contains a group capable of forming an anion (e.g., —COOH), then an inner salt (also referred to as a zwitterion) may be formed.

Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyloxybenzoic, acetic, trifluoroacetic, ascorbic, aspartic, benzoic, camphorsulfonic, cinnamic, citric, edetic, 1,2-ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well-known chemical methods are employed to reversibly render unreactive a functional group, which otherwise would be reactive, under specified conditions. In a chemically protected form, one or more reactive functional groups are in the form of a protected or protecting group (alternatively as a masked or masking group or a blocked or blocking group). By protecting a reactive functional group, reactions involving other unprotected reactive functional groups can be performed, without affecting the protected group; the protecting group may be removed or the masking group transformed, usually in a subsequent step, without substantially affecting the remainder of the molecule. See, for example, *Protective Groups in Organic Synthesis* (T. Green and P. Wuts; 4th Edition; John Wiley and Sons, 2006).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an amine group may be protected, for example, as an amide (—NRCO—R) or a urethane (—NRCO—OR), for example, as: an acetamide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH—Fmoc), as a 6-nitroveratryloxy amide (—NH—Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH—Psec); or, in suitable cases (e.g., cyclic amines), as a nitroxide radical (>N—O·).

Prodrugs

It may be convenient or desirable to prepare, purify, and/or handle the compound in the form of a prodrug. The term "prodrug," as used herein, pertains to a compound, which yields the desired active compound in vivo. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound, which, upon further chemical reaction, yields the active compound (for example, as in antibody directed enzyme prodrug therapy (ADEPT), gene directed enzyme prodrug therapy (GDEPT), lipid directed enzyme prodrug therapy (LIDEPT), etc.). For example, the prodrug may be a sugar derivative or other glycoside conjugate, or may be an amino acid ester derivative.

Compositions

One aspect of the present invention pertains to a composition (e.g., a pharmaceutical composition) comprising an APPAMP compound, as described herein, and a pharmaceutically acceptable carrier, diluent, or excipient.

Another aspect of the present invention pertains to a method of preparing a composition (e.g., a pharmaceutical composition) comprising mixing an APPAMP compound, as described herein, and a pharmaceutically acceptable carrier, diluent, or excipient.

Uses

The APPAMP compounds described herein are useful in the treatment of, for example, proliferative disorders (as "anti-proliferative agents"), cancer (as "anti-cancer agents"), viral infections (as "anti-viral agents"), neurodegenerative diseases (as "anti-neurodegenerative agents"), etc.

Use in Methods of Inhibiting CDK

One aspect of the present invention pertains to a method of inhibiting CDK (e.g., CDK1, CDK2, CDK4, CDK5, CDK6, CDK7, CDK8, CDK9, CDK10, CDK11, CDK12, CDK13, etc.) function (e.g., in a cell), in vitro or in vivo, comprising contacting the cell with an effective amount of an APPAMP compound, as described herein.

One of ordinary skill in the art is readily able to determine whether or not a candidate compound inhibits CDK (e.g., CDK1, CDK2, CDK4, CDK5, CDK6, CDK7, CDK8, CDK9, CDK10, CDK11, CDK12, CDK13, etc.). For example, suitable assays are described herein or are known in the art.

In one embodiment, the method is performed in vitro.

In one embodiment, the method is performed in vivo.

In one embodiment, the APPAMP compound is provided in the form of a pharmaceutically acceptable composition.

Any type of cell may be treated, including adipose, lung, gastrointestinal (including, e.g., bowel, colon), breast (mammary), ovarian, prostate, liver (hepatic), kidney (renal), bladder, pancreas, brain, and skin.

For example, a sample of cells may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Inhibiting Cell Proliferation, Etc.

The APPAMP compounds described herein, e.g., (a) regulate (e.g., inhibit) cell proliferation; (b) inhibit cell cycle progression; (c) promote apoptosis; or (d) a combination of one or more of these.

One aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of an APPAMP compound, as described herein.

In one embodiment, the method is a method of regulating (e.g., inhibiting) cell proliferation (e.g., proliferation of a cell), in vitro or in vivo, comprising contacting a cell with an effective amount of an APPAMP compound, as described herein.

In one embodiment, the method is performed in vitro.

In one embodiment, the method is performed in vivo.

In one embodiment, the APPAMP compound is provided in the form of a pharmaceutically acceptable composition.

Any type of cell may be treated, including lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound regulates (e.g., inhibits) cell proliferation, etc. For example, assays, which may conveniently be used to assess the activity offered by a particular compound are described herein.

For example, a sample of cells (e.g., from a tumour) may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to an APPAMP compound, as described herein, for use in a method of treatment of the human or animal body by therapy, for example, for use a method of treatment of a disorder (e.g., a disease) as described herein.

Use in the Manufacture of Medicaments

Another aspect of the present invention pertains to use of an APPAMP compound, as described herein, in the manufacture of a medicament, for example, for use in a method of treatment, for example, for use a method of treatment of a disorder (e.g., a disease) as described herein.

In one embodiment, the medicament comprises the APPAMP compound.

Methods of Treatment

Another aspect of the present invention pertains to a method of treatment, for example, a method of treatment of a disorder (e.g., a disease) as described herein, comprising administering to a subject in need of treatment a therapeutically-effective amount of an APPAMP compound, as described herein, preferably in the form of a pharmaceutical composition.

Disorders Treated

In one embodiment (e.g., for use in methods of therapy, of use in the manufacture of medicaments, of methods of treatment), the treatment is treatment of: a disorder (e.g., a disease) that is associated with CDK; a disorder (e.g., a disease) resulting from an inappropriate activity of a CDK; a disorder (e.g., a disease) that is associated with CDK mutation; a disorder (e.g., a disease) that is associated with CDK overexpression; a disorder (e.g., a disease) that is associated with upstream pathway activation of CDK; a disorder (e.g., a disease) that is ameliorated by the inhibition (e.g., selective inhibition) of CDK.

In one embodiment (e.g., for use in methods of therapy, of use in the manufacture of medicaments, of methods of treatment), the treatment is treatment of: a proliferative disorder; cancer; a viral infection (e.g., HIV); a neurodegenerative disorder (e.g., Alzheimer's disease, Parkinson's disease); ischaemia; a renal disease; a cardiovascular disorder (e.g., atherosclerosis); or an autoimmune disorder (e.g., rheumatoid arthritis).

Disorders Treated—Disorders Associated with CDK

In one embodiment (e.g., for use in methods of therapy, of use in the manufacture of medicaments, of methods of treatment), the treatment is treatment of a disorder (e.g., a disease) that is associated with CDK (e.g., CDK1, CDK2, CDK4, CDK5, CDK6, CDK7, CDK8, CDK9, CDK10, CDK11, CDK12, CDK13, etc.), especially CDK7.

In one embodiment, the treatment is treatment of: a disorder (e.g., a disease) resulting from an inappropriate activity of a CDK (e.g., CDK1, CDK2, CDK4, CDK5, CDK6, CDK7, CDK8, CDK9, CDK10, CDK11, CDK12, CDK13, etc.), especially CDK7.

In one embodiment, the treatment is treatment of: a disorder (e.g., a disease) that is associated with CDK mutation; CDK overexpression (e.g., as compared to corresponding normal cells; e.g., wherein the overexpression is by a factor of 1.5, 2, 3, 5, 10, 20 or 50); or upstream pathway activation of CDK.

In one embodiment, the treatment is treatment of a disorder (e.g., a disease) that is ameliorated by the inhibition (e.g., selective inhibition) of CDK (e.g., CDK1, CDK2, CDK4, CDK5, CDK6, CDK7, CDK8, CDK9, CDK10, CDK11, CDK12, CDK13, etc.), especially CDK7.

Disorders Treated—Proliferative Disorders

In one embodiment (e.g., for use in methods of therapy, of use in the manufacture of medicaments, of methods of treatment), the treatment is treatment of a proliferative disorder.

The term "proliferative disorder," as used herein, pertains to an unwanted or uncontrolled cellular proliferation of excessive or abnormal cells which is undesired, such as neoplastic or hyperplastic growth.

In one embodiment, the treatment is treatment of: a proliferative disorder characterised by benign, pre-malignant, or malignant cellular proliferation.

In one embodiment, the treatment is treatment of: hyperplasia; a neoplasm; a tumour (e.g., a histocytoma, a glioma, an astrocyoma, an osteoma); cancer; psoriasis; a bone disease; a fibroproliferative disorder (e.g., of connective tissues); pulmonary fibrosis; atherosclerosis; or smooth muscle cell proliferation in the blood vessels (e.g., stenosis or restenosis following angioplasty).

Disorders Treated—Cancer

In one embodiment (e.g., of use in methods of therapy, of use in the manufacture of medicaments, of methods of treatment), the treatment is treatment of cancer.

In one embodiment, the treatment is treatment of cancer metastasis.

Included among cancers are:

(1) Carcinomas, including tumours derived from stratified squamous epithelia (squamous cell carcinomas) and tumours arising within organs or glands (adenocarcinomas). Examples include breast, colon, lung, prostate, ovary.

(2) Sarcomas, including: osteosarcoma and osteogenic sarcoma (bone); chondrosarcoma (cartilage); leiomyosarcoma (smooth muscle); rhabdomyosarcoma (skeletal muscle); mesothelial sarcoma and mesothelioma (membranous lining of body cavities); fibrosarcoma (fibrous tissue); angiosarcoma and haemangioendothelioma (blood vessels); liposarcoma (adipose tissue); glioma and astrocytoma (neurogenic connective tissue found in the brain); myxosarcoma (primitive embryonic connective tissue); mesenchymous and mixed mesodermal tumour (mixed connective tissue types).

(3) Myeloma.

(4) Haematopoietic tumours, including: myelogenous and granulocytic leukaemia (malignancy of the myeloid and granulocytic white blood cell series); lymphatic, lymphocytic, and lymphoblastic leukaemia (malignancy of the lymphoid and lymphocytic blood cell series); polycythaemia vera (malignancy of various blood cell products, but with red cells predominating).

(5) Lymphomas, including: Hodgkin and Non-Hodgkin lymphomas.

(6) Mixed Types, including, e.g., adenosquamous carcinoma; mixed mesodermal tumour; carcinosarcoma; teratocarcinoma.

For example, in one embodiment, the treatment is treatment of breast cancer.

In one embodiment, the cancer is characterised by, or further characterised by, cancer stem cells.

In one embodiment, the cancer is associated with CDK (e.g., CDK1, CDK2, CDK4, CDK5, CDK6, CDK7, CDK8, CDK9, CDK10, CDK11, CDK12, CDK13, etc.), especially CDK7.

In one embodiment, the cancer is characterised by, or further characterised by, inappropriate activity of CDK (e.g., CDK1, CDK2, CDK4, CDK5, CDK6, CDK7, CDK8, CDK9, CDK10, CDK11, CDK12, CDK13, etc.), especially CDK7.

In one embodiment, the cancer is characterised by, or further characterised by, overexpression of CDK (e.g., CDK1, CDK2, CDK4, CDK5, CDK6, CDK7, CDK8, CDK9, CDK10, CDK11, CDK12, CDK13, etc.), especially CDK7.

The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of cell migration (the spread of cancer cells to other parts of the body), the inhibition of invasion (the spread of tumour cells into neighbouring normal structures), the promotion of apoptosis (programmed cell death), death by necrosis, or induction of death by autophagy. The compounds described herein may be used in the treatment of the cancers described herein, independent of the mechanisms discussed herein.

Disorders Treated—Viral Infection

In one embodiment (e.g., for use in methods of therapy, of use in the manufacture of medicaments, of methods of treatment), the treatment is treatment of a viral infection.

In one embodiment, the treatment is treatment of a viral infection by:
 (Group I:) a dsDNA virus, e.g., an adenovirus, a herpesvirus, a poxvirus;
 (Group II:) a ssDNA virus, e.g., a parvovirus;
 (Group III:) a dsRNA virus, e.g., a reovirus;
 (Group IV:) a (+)ssRNA virus, e.g., a picornavirus, a togavirus;
 (Group V:) a (−)ssRNA virus, e.g., an orthomyxovirus, a rhabdovirus;
 (Group VI:) a ssRNA-RT virus, e.g., a retrovirus; or
 (Group VII:) a dsDNA-RT virus, e.g., a hepadnavirus.

As used above: ds: double strand; ss: +strand; (+)ssRNA: +strand RNA; (−)ssRNA: −strand RNA; ssRNA-RT: (+strand)RNA with DNA intermediate in life-cycle.

In one embodiment, the treatment is treatment of: human immunodeficiency virus (HIV); hepatitis B virus (HBV); hepatitis C virus (HCV); human papilloma virus (HPV); cytomegalovirus (CMV); or Epstein-Barr virus (EBV); human herpesvirus 8 (HHV) associated with Kaposi sarcoma; Coxsackievirus B3; Borna virus; influenza virus.

Disorders Treated—Autoimmune Disorders

In one embodiment (e.g., for use in methods of therapy, of use in the manufacture of medicaments, of methods of treatment), the treatment is treatment of an autoimmune disorder.

In one embodiment, the treatment is treatment of: an autoimmune disorder associated with connective tissue, joints, skin, or the eye.

In one embodiment, the treatment is treatment of: rheumatoid arthritis, systemic lupus erythematosus, psoriasis, or Sjogren's syndrome.

Treatment

The term "treatment," as used herein in the context of treating a disorder, pertains generally to treatment of a human or an animal (e.g., in veterinary applications), in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. Treatment as a prophylactic measure (i.e., prophylaxis) is also included.

For example, use with patients who have not yet developed the disorder, but who are at risk of developing the disorder, is encompassed by the term "treatment."

For example, treatment includes the prophylaxis of cancer, reducing the incidence of cancer, alleviating the symptoms of cancer, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents. Examples of treatments and therapies include chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

One aspect of the present invention pertains to a compound as described herein, in combination with one or more (e.g., 1, 2, 3, 4, etc.) additional therapeutic agents, as described below.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Examples of additional agents/therapies that may be co-administered/combined with treatment with the APPAMP compounds described herein include the following:

- an aromatase inhibitor, for example, exemestane (also known as Aromasin), letrozole (also known as Femara), anastrozole (also known as Arimidex), etc.;
- an anti-estrogen, for example, faslodex (also known as Fulvestrant and 101182780), tamoxifen (also known as Nolvadex), hydroxytamoxifen, etc.;
- a Her2 blocker, for example, herceptin, pertuzumab, lapatinib, etc.;
- a cytotoxic chemotherapeutic agent, for example, a taxane (e.g., paclitaxel also known as Taxol; docetaxel also known as Taxotere), cyclophosphamide, an antimetabolite (e.g., carboplatin, capecitabine, gemcitabine, doxorubicin, epirubicin, 5-fluorouracil, etc.), etc.

Thus, in one embodiment, the treatment further comprises treatment (e.g., simultaneous or sequential treatment) with a further active agent which is, e.g., an aromatase inhibitor, an anti-estrogen, a Her2 blocker, a cytotoxic chemotherapeutic agent, etc.

Combination Therapy with an Aromatase Inhibitor and/or an Anti-Estrogen

Estrogen receptor α (ERα) is expressed in 70% of breast tumours and is recognised as the major driver of breast cancer development and progression in these cases. Consequently, ERα is the predominant target for adjuvant therapies in ERα-positive breast cancer. Inhibition of its activity with anti-estrogens and by inhibition of estrogen biosynthesis (e.g., using aromatase inhibitors), reduces relapse and improves patient survival (see, e.g., Osborne, 1998; Cuzick et al., 2010). Tamoxifen (Nolvadex) is an anti-estrogen that acts by competing with estrogen for binding to the estrogen receptor, to inhibit ERα activity. Importantly, many patients with ERα-positive breast cancer relapse on these hormonal therapies, resistant tumours mostly remaining ERα-positive (see, e.g., Ali et al., 2002; Johnston et al., 2003; Ali et al, 2011; Osborne et al., 2011).

Tamoxifen is an exemplifier of the class of anti-estrogen known as selective estrogen receptor modulators (SERMs), which are anti-estrogenic in the breast, but often have estrogen-like activities in other tissues, such as the cardiovascular system, and bone. Tamoxifen has been used widely as first line adjuvant agent for the treatment of ERα-positive breast cancer in pre- and post-menopausal women. Fulvestrant (Faslodex) is an anti-estrogen that competes with estrogen for binding to ERα to prevent its activation, but also promotes down-regulation of the ERα protein. As such, fulvestrant is an exemplifier of the class of anti-estrogens known as selective estrogen recepto downregulators (SERD). Fulvestrant is primarily used in the treatment of ERα-positive breast cancer patients who experience recurrence following treatment with first-line adjuvant agents such as tamoxifen.

Aromatase is a cytochrome P450 enzyme that catalyses the limiting step in conversion of androgens to estrogens. Clinically, anastrozole (Arimidex) and letrozole (Femara) are competitive inhibitors of the aromatase complex, whilst exemestane (Aromasin) is an irreversible inhibitor of aromatase. Aromatse inhibitors act by inhibiting estrogan biosynthesis and thereby levels of circulating estrogens and consequently by limiting estrogen availability they prevent ERα activation.

Estrogen binding to ERα protein occurs in the ligand (hormone) binding domain (LBD), which is C-terminal to the DNA binding domain (DBD), to promote ERα dimerisation, nuclear localisation and binding to DNA in regulatory regions of target genes, to regulate the expression of said target genes. Phosphorylation of ERα provides a key mechanism for regulating ERα activity, including DNA binding and transcription activation. In particular, ERα phosphorylation at serine-118 in a region N-terminal to the DBD that is important for transcription activation by ERα (known as transcription activation function 1 (AF-1), is one of the earlies events in ERα activation. Serine-118 phophorylation is mediated by estrogen stimulated recruitment of the transcription factor complex, TFIIH, which includes CDK7. Estrogen-stimulated TFIIH recruitment to the estrogen-bound LBD allows CDK7-mediated phosphorylation of serine-118, to promote ERα activity. CDK7 over-expression can promote ERα activity under conditions of low estrogen levels, as engendered by aromatse inhibitors, and lead to activation of the tamoxifen-bound ERα (see, e.g., Ali et al., 1993; Chen et al., 2000; Chen et al., 2002).

These findings provide the basis for the use of an APPAMP compound, as described herein, in combination with an aromatase inhibitor or an anti-estrogen, for the treatment of breast cancer patients. Such a combination therapy would be especially useful in the treatment of breast cancer patients following emergence of resistance to the aromatase inhibitor or anti-estrogen. Such a combination therapy would also permit the use of reduced amounts and/or concentrations of the APPAMP compound, the anti-estrogen, and/or the aromatase inhibitor, in order to reduce toxicity.

Studies demonstrating the synergistic effects of the combination of a particular pyrazolo[1,5-a]pyrimidine-5,7-diamine compound (PPDA-001, also referred to as ICEC0942) with an anti-estrogen (4-hydroxytamoxifen or Faslodex) in the estrogen-responsive ERα-positive MCF-7 breast cancer cell line is described in Bondke et al., 2015. The agents acts co-operatively to inhibit the growth of breast cancer cells.

Thus, in one embodiment, the treatment further comprises treatment (e.g., simultaneous or sequential treatment) with a further active agent which is an aromatase inhibitor, for example, exemestane (also known as Aromasin), letrozole (also known as Femara), or anastrozole (also known as Arimidex). In one embodiment, the disorder is breast cancer (e.g., breast cancer which is resistant to said aromatase inhibitor).

Also, in one embodiment, the treatment further comprises treatment (e.g., simultaneous or sequential treatment) with a further active agent which is an anti-estrogen, for example, faslodex (also known as Fulvestrant and ICI182780), tamoxifen (also known as Nolvadex), or hydroxytamoxifen. In one embodiment, the disorder is breast cancer (e.g., breast cancer which is resistant to said anti-estrogen).

Other Uses

The APPAMP compounds described herein may also be used as cell culture additives to inhibit CDK (e.g., CDK1, CDK2, CDK4, CDK5, CDK6, CDK7, CDK8, CDK9, CDK10, CDK11, CDK12, CDK13, etc.).

The APPAMP compounds described herein may also be used as part of an in vitro assay, for example, in order to determine whether a candidate host is likely to benefit from treatment with the compound in question.

The APPAMP compounds described herein may also be used as a standard, for example, in an assay, in order to identify other active compounds, other CDK (e.g., CDK1, CDK2, CDK4, CDK5, CDK6, CDK7, CDK8, CDK9, CDK10, CDK11, CDK12, CDK13, etc.) inhibitors, etc.

Kits

One aspect of the invention pertains to a kit comprising (a) an APPAMP compound as described herein, or a composition comprising an APPAMP compound as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The APPAMP compound or pharmaceutical composition comprising the APPAMP compound may be administered to a subject by any convenient route of administration, whether systemically/peripherally or topically (i.e., at the site of desired action).

Examples of routes of administration include oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for an APPAMP compound to be administered alone, it is preferable to present it as a pharmaceutical formulation (e.g., composition, preparation, medicament) comprising at least one APPAMP compound, as described herein, together with one or more other pharmaceutically acceptable ingredients well known to those skilled in the art, including pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising mixing at least one APPAMP compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005.

The formulations may be prepared by any methods well known in the art of pharmacy. Such methods include the step of bringing into association the compound with a carrier, which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, lozenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or mixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, iso-propyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection) include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additionally contain other pharmaceutically acceptable ingredients, such as anti-oxidants, buffers, preservatives, stabilisers, bacteriostats, suspending agents, thickening agents, and solutes, which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 10 µg/mL, for example from about 10 ng/mL to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use.

Extemporaneous injection solutions and suspensions may be prepared from sterile powders, granules, and tablets.

Dosage

It will be appreciated by one of skill in the art that appropriate dosages of the APPAMP compounds, and compositions comprising the APPAMP compounds, can vary from patient to patient. Determining the optimal dosage will generally involve the balancing of the level of therapeutic benefit against any risk or deleterious side effects. The selected dosage level will depend on a variety of factors including the activity of the particular APPAMP compound, the route of administration, the time of administration, the rate of excretion of the APPAMP compound, the duration of the treatment, other drugs, compounds, and/or materials used in combination, the severity of the disorder, and the species, sex, age, weight, condition, general health, and prior medical history of the patient. The amount of APPAMP compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the APPAMP compound is in the range of about 10 µg to about 250 mg (more typically about 100 µg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

Chemical Syntheses

Methods for the chemical synthesis of the APPAMP compounds are described herein. These and/or other well-known methods may be modified and/or adapted in known ways in order to provide alternative or improved methods of synthesis of the APPAMP compounds.

Abbreviations aq: aqueous;
Boc: tert-butoxycarbonyl;
$Boc_2O$: di-tert-butyl dicarbonate;
br: broad;
ca.: circa;
d: doublet;
$^tBuXPhos$-Pd-G3: [(2-di-tert-butylphosphino-2',4',6'-triisopropyl-1,1'-biphenyl)-2-(2'-amino-1,1'-biphenyl)] palladium(II) methanesulfonate;
DCM: dichloromethane;
dioxane: 1,4-dioxane;
DIPEA: diisopropylethylamine;
EtOAc: ethyl acetate;
EtOH: ethanol;
h: hours;
HPLC: high performance liquid chromatography;
LCMS: liquid chromatography—mass spectrometry;
LiHMDS: lithium hexamethyldisilazide;
m: multiplet;
M: molar, molecular ion;
MeCN: actetonitrile;
MeOH: methanol;
min: minutes;
MS: mass spectrometry;
NCS: N-chlorosuccinimide;
NIS: N-iodosuccinimide;
NMR: nuclear magnetic resonance;
$PdCl_2(dppf)\cdot DCM$: [1,1'-Bis(diphenylphosphino)ferrocene]dichloropalladium(II), complex with dichloromethane;
q: quartet;
RT: room temperature (ca. 20° C.);
$R_T$: retention time;
s: singlet, solid;
SCX: strong cation exchange;
t: triplet;
TFA: trifluoroacetic acid;
THF: tetrahydrofuran.

Other abbreviations are intended to convey their generally accepted meaning.

Nomenclature of structures was generated using 'Structure to Name' conversion from ChemDraw® Professional 15 (PerkinElmer).

General Synthesis

APPAMP compounds may be prepared, for example, by a method illustrated in the following chemical scheme. Formylation of nitrile (I-1) using ethyl formate, followed by condensation of the resultant α-formylnitrile with hydrazine yields aminopyarazole (I-2). Condensation with diethyl malonate, followed by chlorination with phosphorus oxychloride yields pyrazolopyrimidine I-3. Nucleophilic aromatic substitution with an amine, followed by Boc protection yields 5-aminopyrazolopyrimidine I-4, which is subsequently converted to intermediate I-5 using a Buchwald-Hartwig cross-coupling reaction. Boc deprotection of intermediate I-5, for example using TFA, yields compound I-6. Optionally, I-6 is chlorinated using NCS to afford the 6-chloro analogue I-7.

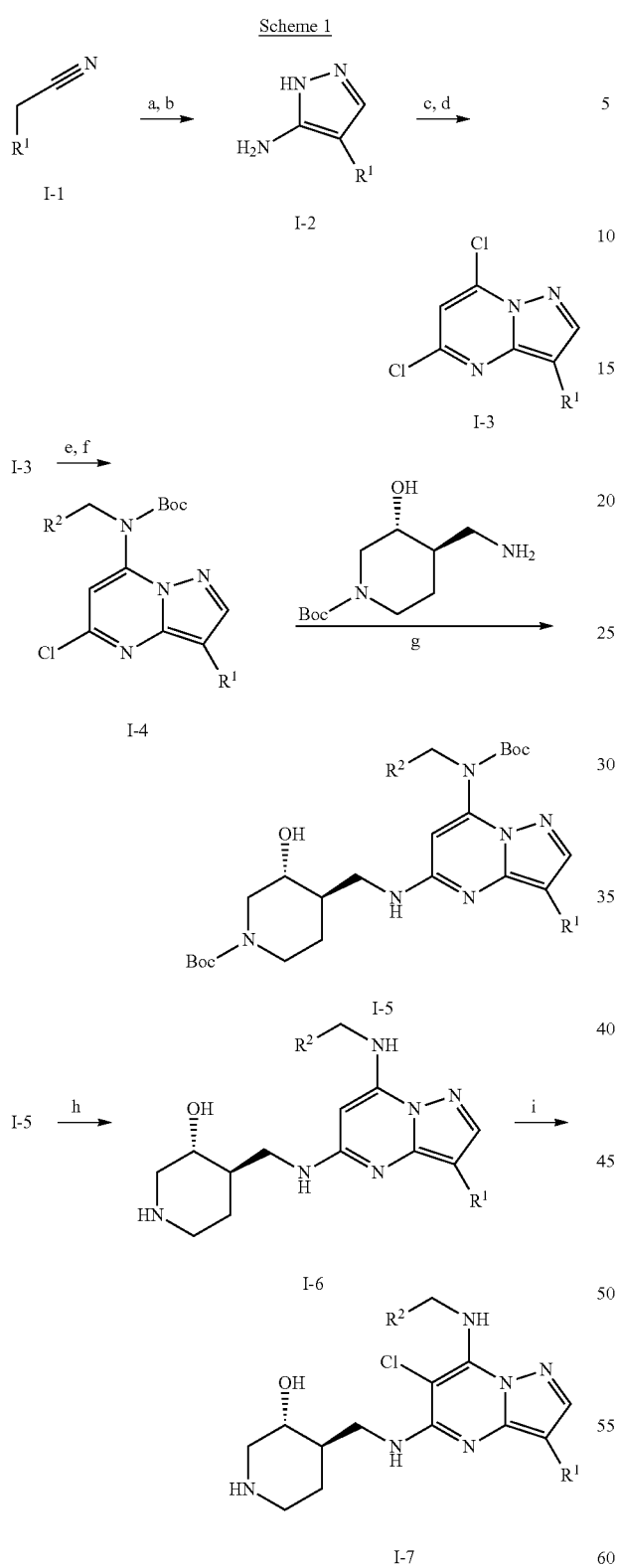

The reactions conditions in the above scheme are as follows: (a)" BuLi, $^i$Pr$_2$NH, EtOCHO, THF, −78° C. to RT; (b) N$_2$H$_4$(aq), AcOH, EtOH, 90° C.; (c) Na(s), EtOH, Diethyl malonate, reflux; (d) POCl$_3$, PhNMe$_2$, 60-90° C.; (e) R$^2$CH$_2$NH$_2$, DIPEA, EtOH, reflux; (f) Boc$_2$O, DMAP, DCM, RT; (g) $^t$BuXPhos-Pd-G3, LiHMDS, THF, 60° C.; (h) TFA, DCM, RT; (i) NCS, DCM, RT.

Alternatively, as illustrated in the following chemical scheme, I-5 can be prepared by iodination of 5,7-dichloropyrazolo[1,5-a]pyrimidine, followed by nucleophilic aromatic substitution with an amine and Boc protection to provide iodoheterocycle I-8, which can be converted to I-5 using a Suzuki-Miyaura coupling reaction.

The reactions conditions in the above scheme are as follows: (a) NIS, MeCN, reflux; (b) R$^2$CH$_2$NH$_2$, DIPEA, EtOH, reflux; (c) Boc$_2$O, DMAP, DCM, RT; (d) PdCl$_2$(dppf)·DCM, K$_3$PO$_4$, PhMe, H$_2$O, 100° C.

Chemical Synthesis Examples

The following examples are provided solely to illustrate the present invention and are not intended to limit the scope of the invention, as described herein.

General Experimental Conditions

All starting materials and solvents were obtained either from commercial sources or prepared according to the literature citation. Reaction mixtures were magnetically stirred unless otherwise indicated.

Column chromatography was performed on an automated flash chromatography system, such as a CombiFlash Rf system, using Grace™ GraceResolv™ pre-packed silica (40 μm) cartridges, unless otherwise indicated.

$^1$H NMR spectra were recorded using a Bruker Avance III spectrometer (400 MHz). Chemical shifts are expressed in parts per million using either the central peaks of the residual protic solvent or an internal standard of tetramethylsilane as references. The spectra were recorded at ambient temperature unless otherwise stated.

Analytical LCMS experiments to determine retention times and associated mass ions were performed using an Agilent 1200 series HPLC system coupled to an Agilent 6110 or 6120 series single quadrupole mass spectrometer running Method 1 or Method 2 described below.

Preparative HPLC purifications were performed using a Waters X-Bridge BEH C18, 5 μm, 19×50 mm column using a gradient of MeCN and 10 mM ammonium bicarbonate (aq). Fractions were collected following detection by UV at a single wavelength measured by a variable wavelength detector.

SCX resin was purchased from Sigma Aldrich or Silicycle and washed with MeOH prior to use.

Analytical Methods

Method 1—Acidic 4 Min Method:

Column: Waters X-Select CSH C18, 2.5 μm, 4.6×30 mm

Detection: UV at 254 nm unless otherwise indicated

MS ionisation: Electrospray

Solvent A: Water/0.1% Formic acid

Solvent B: MeCN/0.1% Formic acid

| Method 1-Gradient | | | |
|---|---|---|---|
| Time | % A | % B | Flow rate (ml/min) |
| 0.0 | 95.0 | 5.0 | 2.5 |
| 3.0 | 5.0 | 95.0 | 2.5 |
| 3.01 | 5.0 | 95.0 | 4.5 |
| 3.6 | 5.0 | 95.0 | 4.5 |
| 3.7 | 95.0 | 5.0 | 2.5 |
| 4.0 | 95.0 | 5.0 | 2.5 |

Method 2—Basic 4 Min Method:

Column: Waters X-Bridge BEH C18, 2.5 μm, 4.6×30 mm

Solvent A: Water/10 mM ammonium bicarbonate

Solvent B: MeCN (other parameters are the same as for Method 1)

Synthesis 1

(3R,4R)-4-(((7-(benzylamino)-3-cyclopropylpyrazolo[1,5-a]pyrimidin-5-yl)amino)methyl)piperidin-3-ol (Compound APPAMP-002)

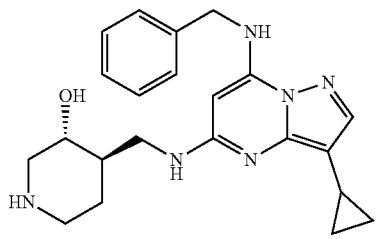 [SMILES: O[C@H]1CNCC[C@@H]1CNc1cc(NCc2ccccc2)n2ncc(C3CC3)c2n1]

Step 1: 5,7-dichloro-3-iodopyrazolo[1,5-a]pyrimidine

A mixture of 5,7-dichloropyrazolo[1,5-a]pyrimidine (6.1 g, 32.4 mmol) and NIS (8.03 g, 35.7 mmol) in MeCN (20 ml) was heated under reflux for 1 h. The mixture was concentrated in vacuo and the residue dissolved in DCM (200 ml) and washed with water (200 ml). The organic phase was dried over $Na_2SO_4(s)$, filtered and concentrated in vacuo. Purification by column chromatography (220 g cartridge, DCM) afforded the title compound (9.1 g, 28.4 mmol, 98% purity) as a crystalline yellow solid. $^1$H NMR (400 MHz, DMSO-$d_6$) δ 8.48 (s, 1H), 7.73 (s, 1H).

Step 2: tert-butyl benzyl(5-chloro-3-iodopyrazolo[1,5-a]pyrimidin-7-yl)carbamate A mixture of the product from Step 1 above (2.00 g, 6.24 mmol, 98% purity), benzylamine (765 μl, 7.01 mmol) and DIPEA (2.23 ml, 12.7 mmol) in dioxane (20 ml) was heated at 80° C. for 2 h. The mixture concentrated in vacuo and the residue dissolved in THF (20 ml). $Boc_2O$ (2.09 g, 9.58 mmol) and DMAP (78 mg, 0.637 mmol) were added to this solution and the resultant mixture was heated at 40° C. for 2 h. The reaction mixture was concentrated in vacuo and the residue was purified by column chromatography (120 g cartridge, 0-50% EtOAc/isohexanes) to afford the title compound (710 mg, 1.44 mmol, 98% purity) as a yellow solid. LCMS (Method 2): $R_T$ 1.73 min, no ionisation.

Step 3: tert-butyl benzyl(5-chloro-3-cyclopropylpyrazolo[1,5-a]pyrimidin-7-yl)carbamate A mixture of cyclopropylboronic acid (70.9 mg, 0.825 mmol), potassium phosphate (350 mg, 1.65 mmol), the product from Step 2 above (400 mg, 0.809 mmol, 98% purity) and $PdCl_2$(dppf)·DCM (13.5 mg, 0.017 mmol) in a mixture of toluene (8 ml) and water (1 ml) was heated at 100° C. for 5 h. The mixture was concentrated in vacuo and the residue purified by column chromatography (40 g cartridge, 0-100% DCM/isohexane) to afford the title compound (225 mg, 0.553 mmol, 98% purity) as a thick yellow gum. $^1$H NMR (400 MHz, DMSO-$d_6$) δ 8.10 (s, 1H), 7.34-7.18 (m, 5H), 7.12 (s, 1H), 5.00 (s, 2H), 1.97 (tt, J=8.4, 5.1 Hz, 1H), 1.28 (s, 9H), 0.99-0.89 (m, 2H), 0.81-0.75 (m, 2H).

Step 4: (3R,4R)-4-(((7-(benzylamino)-3-cyclopropylpyrazolo[1,5-a]pyrimidin-5-yl)amino)methyl)piperidin-3-ol A solution of the product from Step 3 above (220 mg, 0.541 mmol, 98% purity), (3R,4R)-tert-butyl 4-(aminomethyl)-3-hydroxypiperidine-1-carboxylate (152 mg, 0.662 mmol) and tBuBrettPhos-Pd-G3 (23.6 mg, 0.028 mmol) in THF (5 ml) was degassed with $N_2$ for 5 min. LiHMDS (1 M in THF) (607 μl, 0.607 mmol) was added and the mixture degassed for an additional 5 min. The reaction mixture was heated at 60° C. for 0.5 h. The reaction mixture was allowed to cool to RT and was poured into EtOAc (50 ml). The organic phase was washed with water (2×20 ml), dried over $Na_2SO_4$(s), filtered and concentrated in vacuo to afford a brown gum. This material was dissolved in 4 M HCl in dioxane (5 ml) and allowed to stand for 1 h. The mixture was concentrated in vacuo and the residue was loaded onto a column of SCX resin (10 g) in MeOH. The column was washed with MeOH and then the product was eluted with 7 M ammonia in MeOH. The fraction containing the product was concentrated in vacuo and the residue further purified by column chromatography (12 g cartridge, 0-10% (0.7 M ammonia in MeOH)/DCM) to afford the title compound (137 mg, 0.346 mmol, 99% purity) as a white solid.

LCMS (Method 2): m/z 393 (M+H)+, 391 (M−H)− at 1.71 min. $^1$H NMR (400 MHz, DMSO-d6) δ 7.83 (t, J=6.5 Hz, 1H), 7.52 (s, 1H), 7.41-7.30 (m, 4H), 7.30-7.19 (m, 1H), 6.70 (t, J=6.1 Hz, 1H), 5.30 (s, 1H), 5.17 (s, 1H), 4.44 (d, J=6.4 Hz, 2H), 3.61-3.41 (m, 1H), 3.25-3.13 (m, 1H), 3.03 (tt, J=9.6, 4.5 Hz, 1H), 2.91 (dd, J=11.6, 4.5 Hz, 1H), 2.83-2.72 (m, 1H), 2.30 (td, J=12.1, 2.6 Hz, 1H), 2.16 (dd, J=11.6, 9.9 Hz, 1H), 1.97 (s, 1H), 1.71 (tt, J=8.4, 5.2 Hz, 1H), 1.61-1.49 (m, 1H), 1.40-1.26 (m, 1H), 1.22-1.05 (m, 1H), 0.82-0.70 (m, 2H), 0.71-0.56 (m, 2H).

Synthesis 2

(3R,4R)-4-(((3-ethyl-7-((2-fluorobenzyl)amino)pyrazolo[1,5-a]pyrimidin-5-yl)amino)methyl)piperidin-3-ol (Compound APPAMP-001)

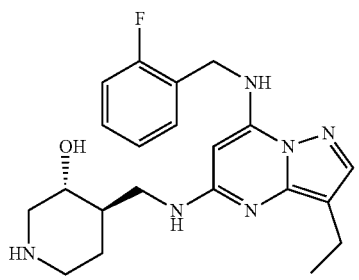 [SMILES: CCc1cnn2c(NCc3ccccc3F)cc(NC[C@H]3CCNC[C@@H]3O)nc12]

Step 1: tert-butyl (5-chloro-3-ethylpyrazolo[1,5-a]pyrimidin-7-yl)(2-fluorobenzyl)carbamate A mixture of 5,7-dichloro-3-ethylpyrazolo[1,5-a]pyrimidine (95 mg, 0.440 mmol), DIPEA (154 µl, 0.879 mmol) and 2-fluorobenzylamine (60.5 mg, 0.484 mmol) in dioxane (5 ml) was heated at 90° C. for 2 h. The reaction mixture was extracted into DCM (20 ml) and washed with water (10 ml). The organic phase was separated and concentrated in vacuo. The residue was dissolved in THF (4 ml) and treated with Boc$_2$O (123 µl, 0.528 mmol), followed by DMAP (2.69 mg, 0.022 mmol). The resultant mixture was stirred at RT for 1 h. The mixture was concentrated in vacuo and the residue purified by column chromatography (12 g cartridge, 0-50% EtOAc/isohexane) to afford the title compound (219 mg) as a clear colourless gum. LCMS (Method 1): m/z 405 (M+H)+ at 2.94 min.

Step 2: (3R,4R)-4-(((3-ethyl-7-((2-fluorobenzyl)amino)pyrazolo[1,5-a]pyrimidin-5-yl)amino)methyl)piperidin-3-ol The product from Step 1 above (140 mg) was reacted with (3R,4R)-tert-butyl 4-(aminomethyl)-3-hydroxypiperidine-1-carboxylate (96 mg, 0.415 mmol), tBuBrettPhos-Pd-G3 (14.8 mg, 0.017 mmol) and LiHMDS (1 M in THF) (346 µl, 0.346 mmol), followed by 4 M HCl in dioxane (5 ml), using the procedure in Synthesis 1 Step 4 to afford the title compound (40 mg, 0.099 mmol, 99% purity) as a cream solid.

LCMS (Method 1): m/z 399 (M+H)+ at 0.98 min. $^1$H NMR (400 MHz, DMSO-d6) δ 7.79 (t, J=6.4 Hz, 1H), 7.66 (s, 1H), 7.40-7.28 (m, 2H), 7.28-7.09 (m, 2H), 6.86-6.69 (m, 1H), 5.44 (s, 1H), 5.16 (s, 1H), 4.51 (d, J=6.4 Hz, 2H), 3.63-3.47 (m, 1H), 3.23-3.13 (m, 1H), 3.03 (tt, J=9.5, 4.4 Hz, 1H), 2.92 (dd, J=11.5, 4.6 Hz, 1H), 2.87-2.77 (m, 1H), 2.49 (q, J=7.5 Hz, 2H), 2.40-2.29 (m, 1H), 2.25-2.11 (m, 1H), 1.65-1.50 (m, 1H), 1.39-1.27 (m, 1H), 1.23-1.12 (m, 1H), 1.18 (t, J=7.5 Hz, 3H).

Synthesis 3

3-(((3-ethyl-5-((((3R,4R)-3-hydroxypiperidin-4-yl)methyl)amino)pyrazolo[1,5-a]pyrimidin-7-yl)amino)methyl)benzonitrile (Compound APPAMP-003)

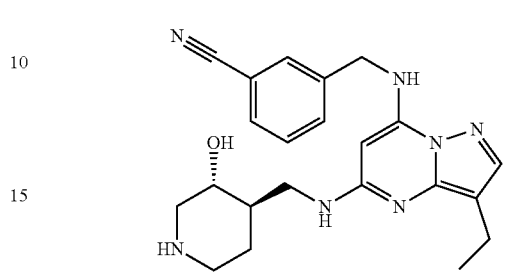

Step 1: tert-butyl (5-chloro-3-ethylpyrazolo[1,5-a]pyrimidin-7-yl)(3-cyanobenzyl)carbamate A mixture of 5,7-dichloro-3-ethylpyrazolo[1,5-a]pyrimidine (136 mg, 0.631 mmol), 3-(aminomethyl)benzonitrile (100 mg, 0.757 mmol) and DIPEA (220 µl, 1.26 mmol) in dioxane (5 ml) was heated at 90° C. for 4 h. The reaction mixture was concentrated in vacuo and the residue dissolved in DCM (10 ml) and washed with water (5 ml). The organic phase was dried over Na$_2$SO$_4$, filtered and concentrated in vacuo. The residue was dissolved in DCM (5 ml) and treated with Boc2O (165 mg, 0.757 mmol), followed by DMAP (3.85 mg, 0.032 mmol). The resultant mixture was stirred at RT for 3 h, then concentrated in vacuo. The residue was purified by column chromatography (12 g column, 0-50% EtOAc/isohexane) to afford the title compound (258 mg, 0.583 mmol, 93% purity). LCMS (Method 1): m/z 434 (M+Na)+, 356 (M+H—C4H8)+ at 2.87 min.

Step 2: 3-(((3-ethyl-5-((((3R,4R)-3-hydroxypiperidin-4-yl)methyl)amino)pyrazolo[1,5-a]pyrimidin-7-yl)amino)methyl)benzonitrile The product from Step 1 above (258 mg, 0.583 mmol, 93% purity) was reacted with (3R,4R)-tert-butyl 4-(aminomethyl)-3-hydroxypiperidine-1-carboxylate (171 mg, 0.742 mmol), tBuBrettPhos-Pd-G3 (26.4 mg, 0.031 mmol) and LiHMDS (1 M in THF) (0.680 ml, 0.680 mmol), followed by 4 M HCl in dioxane (2 ml), using the procedure in Synthesis 1 Step 4, except column chromatography was not carried out and instead the product was purified by preparative HPLC (15-35% MeCN in 10 mM ammonium bicarbonate(aq)) to afford the title compound (31 mg, 0.076 mmol, 99% purity).

LCMS (Method 2): m/z 409 (M+H)+ at 1.59 min. $^1$H NMR (400 MHz, DMSO-d6) δ 7.96 (t, J=6.5 Hz, 1H), 7.84-7.79 (m, 1H), 7.77-7.72 (m, 1H), 7.72-7.68 (m, 1H), 7.66 (s, 1H), 7.57 (t, J=7.7 Hz, 1H), 6.71 (t, J=6.0 Hz, 1H), 5.36 (s, 1H), 5.15 (s, 1H), 4.50 (d, J=6.5 Hz, 2H), 3.61-3.43 (m, 1H), 3.25-3.11 (m, 2H), 3.00 (tt, J=9.5, 4.3 Hz, 1H), 2.90 (dd, J=11.6, 4.6 Hz, 1H), 2.85-2.74 (m, 1H), 2.48 (q, J=7.5 Hz, 2H), 2.37-2.23 (m, 1H), 2.22-2.08 (m, 1H), 1.60-1.49 (m, 1H), 1.40-1.23 (m, 1H), 1.17 (t, J=7.5 Hz, 3H).

Synthesis 4

3-(((6-chloro-3-ethyl-5-((((3R,4R)-3-hydroxypiperidin-4-11)methyl)amino)pyrazolo[1,5-a]pyrimidin-7-yl)amino)methylt)henzonitrile (Compound APPAMP-004)

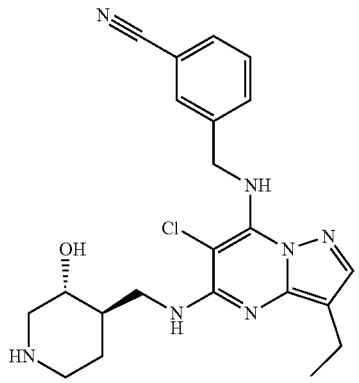 [SMILES: CCc1cnn2c(NCc3cccc(C#N)c3)c(Cl)c(NC[C@H]3CCNC[C@@H]3O)nc12]

A solution of 3-(((3-ethyl-5-((((3R,4R)-3-hydroxypiperidin-4-yl)methyl)amino)pyrazolo[1,5-a]pyrimidin-7-yl)amino)methyl)benzonitrile (Compound APPAMP-003) (Synthesis 3) (122 mg, 0.301 mmol) in DCM (3 ml) was treated with NCS (40.2 mg, 0.301 mmol). The reaction mixture was stirred at RT for 1 h. The reaction mixture was concentrated in vacuo and the residue was purified by preparative HPLC (20-50% MeCN in 10 mM ammonium bicarbonate(aq)) to afford the title compound (17 mg, 0.038 mmol, 98% purity) as a yellow powder.

LCMS (Method 2): m/z 440 (M+H)+ at 1.90 min. 1H NMR (400 MHz, DMSO-d6) δ 7.84-7.74 (m, 2H), 7.72 (s, 1H), 7.72-7.67 (m, 1H), 7.66-7.59 (m, 1H), 7.53 (t, J=7.7 Hz, 1H), 6.87-6.77 (m, 1H), 5.17 (d, J=4.4 Hz, 1H), 5.13 (d, J=7.1 Hz, 2H), 3.66-3.50 (m, 1H), 3.30-3.20 (m, 1H), 3.19-3.06 (m, 1H), 2.92 (dd, J=11.6, 4.6 Hz, 1H), 2.84-2.75 (m, 1H), 2.50 (q, J=7.6 Hz, 2H), 2.38-2.26 (m, 1H), 2.23-2.11 (m, 1H), 1.66-1.53 (m, 1H), 1.54-1.41 (m, 1H), 1.18 (t, J=7.5 Hz, 3H), 1.18-1.04 (m, 1H).

Biological Methods and Data
Biological Methods
Method 1: CDK2 $IC_{50}$
Materials and solutions:
HEPES (Sigma, H3375).
Sodium orthovanadate (Sigma, 450243).
DTT (Sigma).
$MgCl_2$ (Sigma, M1028).
PEG-20000 (Sigma, 95172).
ADP-Glo (Promega, V9102, includes ATP).
Human CDK2/cycE1 (ProQinase, 0050-0055-1).
Histone $H_1$ (Merck Millipore, 14-155).
Assay Procedure:

A reaction mixture (6 μL) containing the following components was prepared: 60 mM HEPES (60 mM, pH 7.5), sodium orthovanadate (3 μM), PEG-20000 (50 μg/mL), DTT (1.2 mM), $MgCl_2$ (3 mM), purified human CDK2/cycE1 (4 μg/mL), histone H1 (50 μg/mL), ATP (20 μM) and test compound at the appropriate concentration such that the final concentration of DMSO was 1% w/w. The reaction mixture was incubated at 30° C. for 75 min and then stopped by the addition of ADP-Glo Reagent (6 μL). The reaction was incubated at 25° C. for 1 h to deplete the remaining ATP. Subsequently, Kinase Detection Reagent (12 μL) was added and the reaction was allowed to proceed for 1 h at 25° C. before analysis by luminescence measurement using an Envision Plate Reader (Perkin Elmer).

Method 2: CDK7 $IC_{50}$
Materials and Solutions:
In addition to those mentioned above for Method 1:
CDK7/cycH/MAT1 (ProQinase, 0366-0360-4).
$MnCl_2$ (Sigma, M1787).
CDKtide (SignalChem, C06-58).
Assay Procedure:

A reaction mixture (6 μL) containing the following components was prepared: 60 mM HEPES (60 mM, pH 7.5), sodium orthovanadate (3 μM), PEG-20000 (50 μg/mL), DTT (1.2 mM), $MgCl_2$ (3 mM), $MnCl_2$ (3 mM), purified human CDK7/cycH/MAT1 (4 μg/mL), CDKtide (10 μM), ATP (8 μM) and test compound at the appropriate concentration such that the final concentration of DMSO was 1% w/w. The reaction mixture was incubated at 30° C. for 30 min and then stopped by the addition of ADP-Glo Reagent (6 μL). The reaction was incubated at 25° C. for 1 h to deplete the remaining ATP. Subsequently, Kinase Detection Reagent (12 μL) was added and the reaction was allowed to proceed for 1 h at 25° C. before analysis by luminescence measurement using an Envision Plate Reader (Perkin Elmer).

Method 3: CDK9 $IC_{50}$
Materials and Solutions:
In addition to those mentioned above for Method 1:
Human CDK9/cycK (Promega, V4104).
CDKtide (SignalChem, C06-58).
Assay Procedure:

A reaction mixture (6 μL) containing the following components was prepared: 60 mM HEPES (60 mM, pH 7.5), sodium orthovanadate (3 μM), PEG-20000 (50 μg/mL), DTT (1.2 mM), $MgCl_2$ (3 mM), purified human CDK9/cycK (2.5 μg/mL), CDKtide (35 μM), ATP (8 μM) and test compound at the appropriate concentration such that the final concentration of DMSO was 1% w/w. The reaction mixture was incubated at 30° C. for 60 min and then stopped by the addition of ADP-Glo Reagent (6 μL). The reaction was incubated at 25° C. for 1 h to deplete the remaining ATP. Subsequently, Kinase Detection Reagent (12 μL) was added and the reaction was allowed to proceed for 1 h at 25° C. before analysis by luminescence measurement using an Envision Plate Reader (Perkin Elmer).

Method 4: Human Plasma Protein Binding (PPB)
Materials and solutions:
Human Plasma (Sera Labs, HMHPLLIHP).
Bupropion hydrochloride (Sigma, B102).
DPBS (Sigma, D8537).
Formic Acid (Sigma, F0507).
RED Device Single Use (Life Technologies, 90006).
Internal standard solution preparation: A solution of bupropion hydrochloride (50 μL, 10 mM in DMSO) was combined with 0.1% formic acid (1 mL) in acetonitrile (1000 mL).
Assay Procedure:

Once frozen plasma was defrosted and adjusted to pH 7.4 using 1 M lactic acid solution and a portion of this mixture (792 μL) combined with each test compound solution (8 μL, 0.5 mM in DMSO). Portions of the resultant spiked plasma (200 μL) were added to sample compartments of the RED device. DBPS (350 μL) was added to each corresponding buffer compartment. An initial sample (50 μL) was taken and then the RED plate was sealed and incubated at 37° C. for 240 min on an orbital shaker (200 rpm) in a humidified $CO_2$ (5%) atmosphere, alongside plasma and DBPS samples. Each sample well was treated with internal standard solution (300 µL). Aliquots (50 µL) were removed from each buffer well and sample well and replaced with incubated plasma (50 µL) or incubated DPBS (50 µL) respectively. The plate was sealed and centrifuged (3500 rpm, 15 min). Aliquots of the supernatant (100 µL) were combined with water (50 µL) for analysis using a Waters TQS Mass Spectrometer.

Method 5: MDCK-MDR1 Efflux Ratio

Materials and solutions:

MDCK/MDR1 Ready™ cell plate (Readycell).

High Glucose Cell Culture Medium (Sigma, D5671) supplemented with: 10% FBS, 1% Glutamine 200 mM, 1% Penicillin (10,000 U/mL)—Streptomycin (10 mg/mL).

HBSS Buffer (Gibco, 14065-049).

Internal standard: 0.5 µM Bupropion in acetonitrile/0.1% formic acid (aq) (1:1 v/v).

Assay Procedure:

HBSS assay buffer was prepared at pH 7.4 and warmed to 37° C. The cell culture media was removed from the Readycell plate. The Basal cells were washed with HBSS buffer (3×225 µL) and the Apical cells were washed with HBSS buffer (3×75 µL). The cells were warmed to 37° C. in a humidified $CO_2$ (5%) atmosphere and shaken at 250 rpm for 30 min. Compound and standard solutions were prepared by diluting each compound (10 µL, 1 mM in DMSO) with HBSS (990 µL). The buffer was carefully removed from the Basal cell plate, followed by the Apical cell plate. HBSS buffer (225 µL) and compound solution (250 µL) were added to the Basal cell plate. An aliquot (25 µL) of the solutions were combined with internal standard (75 µL) and refrigerated for use as the t=0 h sample. HBSS buffer (75 µL) and compound solution (100 µL) were added to the Apical cell plate. An aliquot (25 µL) was taken and processed in the same manner as for the Basal cell plate. The cells were warmed to 37° C. in a humidified $CO_2$ (5%) atmosphere and shaken at 250 rpm for 2 h. After incubation, an aliquot (25 µL) of each Basal and Apical solution was combined with internal standard (75 µL), sealed and centrifuged (3500 rpm, 15 min). Aliquots of the supernatant (50 µL) were combined with water (50 µL) for analysis, along with the t=0 h samples, using a Waters TQS Mass Spectrometer.

Method 6: MDCK-BCRP Efflux Ratio

Essentially the same as Method 5, but using MDCK/BCRP Ready™ cell plates (Readycell) in place of MDCK/MDR1 plates.

Biological Data

The APPAMP compounds were assessed using the biological methods described above.

The following reference compound (REF-001) was also assessed, for comparison purposes.

The resulting data are summarized in the following tables.

TABLE 1

Biochemical Assay Data

| Cmpd No. | CDK2 $IC_{50}$ (nM) | CDK7 $IC_{50}$ (nM) | CDK9 $IC_{50}$ (nM) |
| --- | --- | --- | --- |
| REF-001 | 660 | 34 | 320 |
| APPAMP-001 | 640 | 13 | 200 |
| APPAMP-002 | 770 | 33 | 210 |
| APPAMP-003 | 190 | 8.9 | 22 |
| APPAMP-004 | 2400 | 4.2 | 130 |

TABLE 2

Additional Assay Data

| Cmpd No. | Human PPB (%) | MDCK-MDR1 Efflux Ratio [1] | MDCK-BCRP Efflux Ratio [1] |
| --- | --- | --- | --- |
| REF-001 | 93 | 33 | 32 |
| APPAMP-001 | 85 | 2 | 5 |
| APPAMP-002 | 83 | 5.7 | 2 |
| APPAMP-003 | ND | ND | ND |
| APPAMP-004 | ND | ND | ND |

Comparisons

CDK7 is a key target. Potency for this key target is highly desirable.

The compounds have similar or better or substantially better CDK7 biochemical potency, as compared with REF-001:

TABLE 3

CDK7 Potency: Comparison with REF-001

| Cmpd No. | CDK7 $IC_{50}$ (nM) | Improvement vs. REF-001 (fold) |
| --- | --- | --- |
| REF-001 | 34 | |
| APPAMP-004 | 4.2 | 8.10 |
| APPAMP-003 | 8.9 | 3.82 |
| APPAMP-001 | 13 | 2.62 |
| APPAMP-002 | 33 | 1.03 |

Compounds with greater selectivity for CDK7 vs. CDK2 are expected to provide a higher therapeutic index and/or show greater selectivity towards cells in the disease state as compared to normal tissue. Improved selectivity for CDK7 vs. CDK2 is highly desirable.

The compounds have better or substantially better selectivity for CDK7 vs. CDK2, as compared with REF-001:

| REF-001 Bondke et al., 2015 (PPDA-001) | (3R,4R)-4-(((7-(benzylamino)-3-isopropylpyrazolo[1,5-a]pyrimidin-5-yl)amino)methyl)piperidin-3-ol | 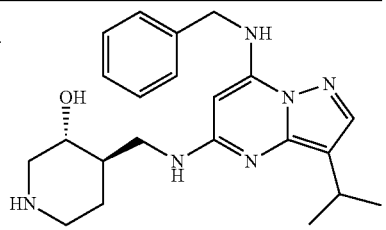 |
| --- | --- | --- |

TABLE 4

CDK2/CDK7 Selectivity: Comparison with REF-001

| Cmpd No. | CDK2 IC$_{50}$ (nM) | CDK7 IC$_{50}$ (nM) | Ratio CDK2/CDK7 | Improvement vs. REF-001 (fold) |
|---|---|---|---|---|
| REF-001 | 660 | 34 | 19 | |
| APPAMP-004 | 2400 | 4.2 | 571 | 29.4 |
| APPAMP-001 | 640 | 13 | 49 | 2.54 |
| APPAMP-002 | 770 | 33 | 23 | 1.20 |
| APPAMP-003 | 190 | 8.9 | 21 | 1.10 |

If a compound has a higher free fraction, then more of the compound is available to interact with a target as opposed to being bound to plasma proteins. A higher free fraction should result in increased in vivo potency, and should permit a lower dose to achieve pharmacological activity. A higher free fraction is highly desirable.

The compounds have substantially higher free fraction in human plasma (i.e., 1—Human PPB), as compared with REF-001:

TABLE 5

Free Fraction: Comparison with REF-001

| Cmpd No. | Human PPB (%) | Free Fraction | Improvement vs. REF-001 (fold) |
|---|---|---|---|
| REF-001 | 93 | 0.07 | |
| APPAMP-002 | 83 | 0.17 | 2.43 |
| APPAMP-001 | 85 | 0.15 | 2.14 |
| APPAMP-003 | ND | ND | ND |
| APPAMP-004 | ND | ND | ND |

Efflux transporters are implicated in cancer drug resistance mechanisms. Lower susceptibility to efflux transporters is recognized as an advantage in cancer therapy. A low efflux ratio is highly desirable.

The compounds have substantially lower efflux ratio in both MDCK-MDR1 and MDCK-BCRP cells, as compared with REF-001:

TABLE 6

MDCK-MDR1 Efflux Ratio: Comparison with REF-001

| Cmpd No. | MDCK-MDR1 Efflux Ratio | Improvement vs. REF-001 (fold) |
|---|---|---|
| REF-001 | 33 | |
| APPAMP-001 | 2 | 16.50 |
| APPAMP-002 | 5.7 | 5.79 |
| APPAMP-003 | ND | ND |
| APPAMP-004 | ND | ND |

TABLE 7

MDCK-BCRP Efflux Ratio: Comparison with REF-001

| Cmpd No. | MDCK-BCRP Efflux Ratio | Improvement vs. REF-001 (fold) |
|---|---|---|
| REF-001 | 32 | |
| APPAMP-002 | 2 | 16.00 |
| APPAMP-001 | 5 | 6.40 |
| APPAMP-004 | ND | ND |
| APPAMP-003 | ND | ND |

As illustrated in the following table, each of the compounds is substantially better than REF-001 in at least one respect, and often in several respects.

TABLE 8

Summary: Improvement vs. REF-001 (fold)

| | APPAMP-001 | APPAMP-002 | APPAMP-003 | APPAMP-004 |
|---|---|---|---|---|
| CDK7 Potency | 2.62 | 1.03 | 3.82 | 8.10 |
| Ratio CDK2/CDK7 | 2.54 | 1.20 | 1.10 | 29.4 |
| Free Fraction | 2.14 | 2.43 | ND | ND |
| MDCK-MDR1 Efflux Ratio | 16.50 | 5.79 | ND | ND |
| MDCK-BCRP Efflux Ratio | 16.00 | 6.40 | ND | ND |

The foregoing has described the principles, preferred embodiments, and modes of operation of the present invention. However, the invention should not be construed as limited to the particular embodiments discussed. Instead, the above-described embodiments should be regarded as illustrative rather than restrictive. It should be appreciated that variations may be made in those embodiments by workers skilled in the art without departing from the scope of the present invention.

REFERENCES

A number of publications are cited herein in order to more fully describe and disclose the invention and the state of the art to which the invention pertains. Full citations for these references are provided below.

Each of these references is incorporated herein by reference in its entirety into the present disclosure, to the same extent as if each individual reference was specifically and individually indicated to be incorporated by reference.

Alarcon et al., 2009, *Cell*, Vol. 139, pp. 757-769.
Ali et al, 2011, *Annu. Rev. Med.*, Vol. 62, pp. 217-232.
Ali et al., 1993, *The EMBO Journal*, Vol. 12, pp. 1153-1160.
Ali et al., 2002, *Nat. Rev. Cancer*, Vol. 2, pp. 101-112.
Ashton et al., 2004, International Patent Application Publication No. WO 2004/069162 A2, published 19 Aug. 2004.
Backer et al., 2004, *Curr. Pharm. Des.*, Vol. 10, No. 23, pp. 2827-2837.
Bartkowiak et al., 2010, *Gene Dev.*, Vol. 24, pp. 2303-2316.
Bastien et al., 2000, *J. Biol. Chem.*, Vol. 275, pp. 21896-21904.
Blazek et al., 2011, *Gene Dev.*, Vol. 25, pp. 2158-2172.
Bondke et al., 2015, International Patent Application Publication No. WO 2015/124941 A1, published 27 Aug. 2015.
Borg et al., 2000, *JNCI*, Vol. 92, No. 15, pp. 1260-1266.
Bosmans et al., 2005, International Patent Application Publication No. WO 2005/000838 A1, published 6 Jan. 2005.
Chen et al., 2000, *Molecular Cell*, Vol. 6, pp. 127-137.
Chen et al., 2002, *Oncogene*, Vol. 21, pp. 4921-4931.
Cheng et al., 2012, *Mol. Cell. Biol.*, Vol. 32, pp. 4691-4704.
Chymkowitch et al., 2011, *EMBO J.*, Vol. 30, pp. 468-479.
Claudio et al., 2006, *J. Cell. Physiol.*, Vol. 208, pp. 602-612.
Cuzick et al., 2010, *Lancet Oncol.*, Vol. 11, pp. 1135-1141.
Drogat et al., 2012, *Cell Rep.*, Vol. 2, pp. 1068-1076.
Dhariwala et al., 2008, *Cell. Mol. Neurobiol.*, Vol. 3, pp. 351-369.

Fisher et al., 1994, *Cell*, Vol. 78, pp. 713-724.
Ganuza et al., 2012, *EMBO J.*, Vol. 31, pp. 2498-2510.
Gijsen et al., 2008, *Tetrahedron*, Vol. 64, pp. 2456-2464.
Gordon et al., 2010, *Mol. Endocrinol.*, Vol. 24, pp. 2267-2280.
Guzi et al., 2004, International Patent Application Publication No. WO 2004/022561 A1, published 18 Mar. 2004.
Hansson, 2010. *Adv. Exp. Med. Biol.*, Vol. 685, pp. 134-145.
Hong et al., 1997, *Tetrahedron Letters*, Vol. 38, pp. 5607-5610.
Hong et al., 2018, *J. Cell. Mol. Med.*, Vol. 22, No. 2, pp. 1292-1301.
Jogalekar et al., 2008, International Patent Application Publication No. WO 2008/151304 A1, published 11 Dec. 2008.
Jogalekar et al., 2010, US Patent Publication No. 2010/0261683 A1, published 14 Oct. 2010.
Jogalekar et al., 2011, U.S. Pat. No. 8,067,424 B2, granted 29 Nov. 2011.
Johnston et al., 2003, Nat. Rev. Cancer, Vol. 3, pp. 821-831.
Jones et al., 2007, *Cell*, Vol. 128, pp. 683-692.
Kataoka et al., 2004, International Patent Application Publication No. WO 2004/076458 A1, published 10 Sep. 2004.
Knockaert et al., 2002, *Trends Pharmacol. Sci.*, Vol. 23, pp. 417-425.
Ko et al., 1997, *Mol. Cell. Biol.*, Vol. 17, No. 12, pp. 7220-7229.
Kolb et al., 1994, *Chem. Rev.*, Vol. 94, pp. 2483-2547.
Larochelle et al., 2007, *Mol. Cell*, Vol. 25, pp. 839-850.
Larochelle et al., 2012, *Nature Struct. Biol. Mol. Biol.*, Vol. 19, pp. 1108-1115.
Iorns et al., 2008, *Cancer Cell*, Vol. 13, pp. 91-104.
Lu et al., 1995, *Nature*, pp. 358, pp. 641-645.
Lu et al., 1997, *Mol. Cell. Biol.*, Vol. 17, pp. 5923-5934.
Malumbres et al., 2001, *Nature Rev. Cancer*, Vol. 1, pp. 222-231.
Malumbres et al., 2009, *Nature Cell Biology*, Vol. 11, pp. 1275-1276.
Malumbres et al., 2009, *Nature Reviews Cancer*, Vol. 9, pp. 153-166.
Marshall et al., 2006, *Nephron. Exp. Nephrol.*, Vol. 102, No. 2, pp. e39-e48.
Monaco et al., 2005, *Front. Biosci.*, Vol. 10, No. 1, pp. 143-159.
Morgan, 1995, *Nature*, Vol. 374, pp. 131-134.
Moriarty et al., 2001, International Patent Application Publication No. WO 2001/047897 A1, published 5 Jul. 2001.
Nagel et al., 1984, *Angew. Chemie*, Vol. 96, pp. 425-426.
Ortega et al, 2002, *Biochim. Biophys. Acta*, Vol. 1602, pp. 73-87.
Osborne et al., 2011, Annu. Rev. Med., Vol. 62, pp. 233-247.
Osborne, 1998, *The New England Journal of Medicine*, Vol. 339, pp. 1609-1618.
Parratt et al., 2004, International Patent Application Publication No. WO 2004/087707 A1, published 14 Oct. 2004.
Pines, 1995, *Biochem. J.*, Vol. 308, pp. 697-711.
Radhakrishnan et al., 2006, *Cell Cycle*, Vol. 5, pp. 519-521.
Rochette-Egly et al., 1997, *Cell*, Vol. 90, pp. 97-107.
Sengupta et al., 2012, International Patent Application Publication No. WO 2012/059932 A1, published 10 May 2012.
Serizawa et al., 1995, *Nature*, Vol. 374, pp. 280-282.
Shiekhattar et al., 1995, *Nature*, Vol. 374, pp. 283-287.
Sherr et al., 1995, *Genes Dev.*, Vol. 9, pp. 1149-1163.
Skehan et al., 1990, *J. Natl. Cancer Inst.*, Vol. 82, pp. 1107-1112.
Vince et al., 1991, *J. Med. Chem.*, Vol. 34, pp. 2787-2797.
Wang et al., 2008, *Trends Pharmacol. Sci.*, Vol. 29, pp. 302-312.
Xu et al., 2011, *J. Genet. Genomics*, Vol. 38, pp. 439-452.
Xu et al., 2011, *Tetrahedron Letters*, Vol. 52, pp. 3266-3270.
Yu et al., 2012, *Oncol. Rep.*, Vol. 27, pp. 1266-1276.
Zuo et al., 1996, *Nature Genetics*, Vol. 12, pp. 97-99.

The invention claimed is:

1. A compound selected from compounds of the following formulae, or a pharmaceutically acceptable salt thereof:

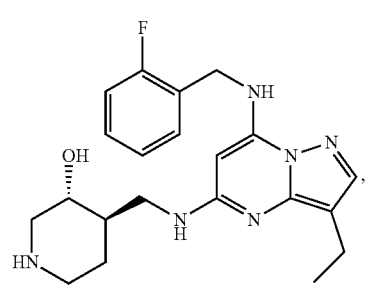

(APPAMP-001)

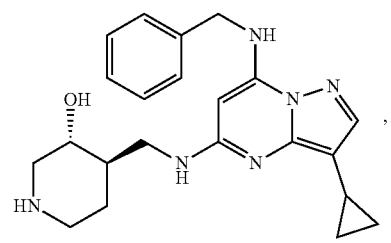

(APPAMP-002)

-continued (APPAMP-003)

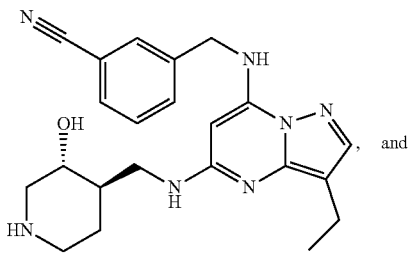

, and

2. A compound according to claim 1, which is a compound of the following formula, or a pharmaceutically acceptable salt thereof:

(APPAMP-001)

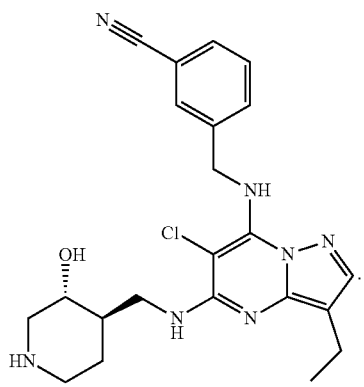

3. A compound according to claim 1, which is a compound of the following formula, or a pharmaceutically acceptable salt thereof:

(APPAMP-002)

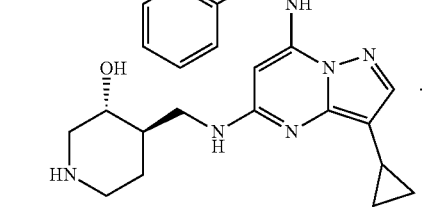

4. A compound according to claim 1, which is a compound of the following formula, or a pharmaceutically acceptable salt thereof:

(APPAMP-003)

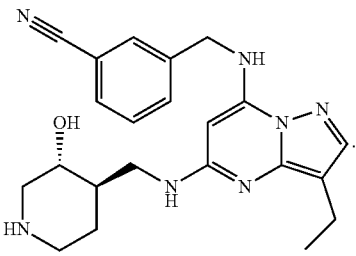

5. A compound according to claim 1, which is a compound of the following formula, or a pharmaceutically acceptable salt thereof:

(APPAMP-004)

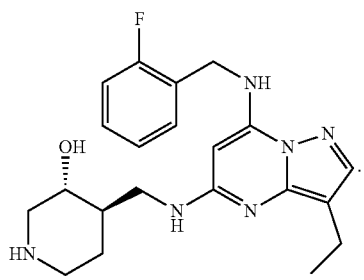

6. A composition comprising a compound according to claim 1, and a pharmaceutically acceptable carrier or diluent.

* * * * *

SEQUENCE LISTING

```
<160> NUMBER OF SEQ ID NOS: 1

<210> SEQ ID NO 1
<211> LENGTH: 7
<212> TYPE: PRT
<213> ORGANISM: Unknown
<220> FEATURE:
<223> OTHER INFORMATION: Mammalian

<400> SEQUENCE: 1

Tyr Ser Pro Thr Ser Pro Ser
1               5
```